US009492312B2

(12) United States Patent
Cappiello et al.

(10) Patent No.: US 9,492,312 B2
(45) Date of Patent: Nov. 15, 2016

(54) METHODS AND APPARATUS FOR INSERTING A DEVICE OR PHARMACEUTICAL INTO A BODY CAVITY

(71) Applicant: Bioceptive, Inc., New Orleans, LA (US)

(72) Inventors: Benjamin Cappiello, New Orleans, LA (US); Shuchi Priye Khurana, Metairie, LA (US); Clarence B. Kemper, III, Baton Rouge, LA (US); Krista A. Wohlfeil, Baton Rouge, LA (US); Bota A. Tastanova, Baton Rouge, LA (US); Mark J. Gabriel, Baton Rouge, LA (US); Catharine Z. Dolese, Baton Rouge, LA (US)

(73) Assignee: Bioceptive, Inc., New Orleans, LA (US)

( * ) Notice: Subject to any disclaimer, the term of this patent is extended or adjusted under 35 U.S.C. 154(b) by 184 days.

(21) Appl. No.: 13/863,734

(22) Filed: Apr. 16, 2013

(65) Prior Publication Data

US 2013/0291872 A1  Nov. 7, 2013

Related U.S. Application Data

(63) Continuation of application No. PCT/US2011/056688, filed on Oct. 18, 2011.

(60) Provisional application No. 61/394,120, filed on Oct. 18, 2010.

(51) Int. Cl.
*A61F 6/18* (2006.01)
*A61K 9/00* (2006.01)
(Continued)

(52) U.S. Cl.
CPC .............. *A61F 6/18* (2013.01); *A61K 9/0039* (2013.01); *A61B 17/4241* (2013.01); *A61B 2017/00566* (2013.01); *A61B 2017/308* (2013.01)

(58) Field of Classification Search
CPC .............. A61F 6/00; A61F 6/06; A61F 6/12; A61F 6/14; A61F 6/142; A61F 6/144; A61F 6/18; A61K 9/0039; A61B 17/4241; A61B 2017/00561; A61B 2017/00566; A61B 2017/306; A61B 2017/308; A61B 17/42; A61B 17/44; A61B 2017/4216; A61B 2017/4225; A61B 1/303; A61B 2090/036
USPC .......................... 604/118–121, 68, 301, 302
See application file for complete search history.

(56) References Cited

U.S. PATENT DOCUMENTS 3,750,662 A   8/1973   Lerner
3,771,520 A   11/1973  Lerner
(Continued)

FOREIGN PATENT DOCUMENTS

CA   2857529   6/2013
EP   0513228   11/1999
(Continued)

OTHER PUBLICATIONS

Office Action for Australian Application No. 2011317256, dated Apr. 7, 2014.
Supplementary European Search Report for European Application No. 11834981, mailed Mar. 7, 2014.
Office Action for Chinese Application No. 201180050217.8, issued Dec. 8, 2014, 11 pages.
(Continued)

*Primary Examiner* — Victoria J Hicks
*Assistant Examiner* — Raymond E Harris
(74) *Attorney, Agent, or Firm* — Cooley LLP

(57) ABSTRACT

In some embodiments, an implant delivery device can include a housing defining a housing passageway. A distal end of the housing can flexibly couple to a head that can define a head passageway. Collectively, the housing passageway and the head passageway can define an insertion passageway such that, at least a portion of the insertion passageway is nonlinear. The implant delivery device can include at least one insertion member having a distal end configured to be removably coupled to an implant. The insertion member can be disposed within the housing such that, at least a portion of a proximal end of the insertion member is housed within the housing. The insertion member can be configured to bend, pivot, and/or rotate and move within a portion of the insertion passageway to convey the implant to a target tissue.

25 Claims, 29 Drawing Sheets

(51) Int. Cl.
  *A61B 17/42* (2006.01)
  *A61B 17/00* (2006.01)
  *A61B 17/30* (2006.01)

(56) References Cited

U.S. PATENT DOCUMENTS

| | | | |
|---|---|---|---|
| 3,783,861 | A | 1/1974 | Abramson |
| 3,794,025 | A | 2/1974 | Lerner |
| 3,842,826 | A | 10/1974 | Nolan |
| 3,845,761 | A | 11/1974 | Zaffaroni |
| 3,857,391 | A | 12/1974 | Lerner |
| 3,880,156 | A | 4/1975 | Hoff |
| 3,913,573 | A | 10/1975 | Gutnick |
| 3,918,444 | A | 11/1975 | Hoff et al. |
| 3,918,445 | A | 11/1975 | Okamoto et al. |
| 3,965,891 | A | 6/1976 | Lerner |
| 3,994,291 | A | 11/1976 | Salmasian |
| 4,005,707 | A | 2/1977 | Moulding, Jr. |
| 4,018,220 | A | 4/1977 | Emmett |
| 4,117,838 | A | 10/1978 | Hasson |
| 4,143,656 | A | 3/1979 | Holmes |
| 4,228,798 | A | 10/1980 | Deaton |
| 4,341,728 | A | 7/1982 | Robertson et al. |
| 4,459,139 | A | 7/1984 | vonReis et al. |
| 4,549,652 | A | 10/1985 | Free |
| 4,658,810 | A | 4/1987 | Bauer |
| 4,708,134 | A | 11/1987 | Wildemeersch |
| 4,711,637 | A | 12/1987 | Leigh et al. |
| 4,949,732 | A | 8/1990 | Spoon et al. |
| 4,961,436 | A | 10/1990 | Koch |
| 4,963,094 | A | 10/1990 | Meyer |
| 5,230,704 | A | 7/1993 | Moberg et al. |
| 5,259,836 | A | 11/1993 | Thurmond et al. |
| 5,370,129 | A * | 12/1994 | Diaz et al. .............. 128/839 |
| 5,494,047 | A | 2/1996 | Van Os |
| 5,540,700 | A | 7/1996 | Rowden et al. |
| 5,643,285 | A | 7/1997 | Rowden et al. |
| RE35,636 | E | 10/1997 | Diaz et al. |
| 5,685,864 | A * | 11/1997 | Shanley ............... A61B 5/1433 604/187 |
| 5,785,053 | A * | 7/1998 | Macandrew et al. ......... 128/840 |
| 5,842,474 | A | 12/1998 | Blyskal et al. |
| 5,935,098 | A | 8/1999 | Blaisdell et al. |
| 6,318,407 | B1 | 11/2001 | Kohn et al. |
| 6,526,979 | B1 | 3/2003 | Nikolchev et al. |
| 6,588,429 | B1 | 7/2003 | Wildemeersch |
| 6,634,361 | B1 | 10/2003 | Nikolchev et al. |
| 6,679,266 | B2 | 1/2004 | Nikolchev et al. |
| 6,686,020 | B2 | 2/2004 | Sakuma |
| 6,705,323 | B1 | 3/2004 | Nikolchev et al. |
| 6,712,810 | B2 | 3/2004 | Harrington et al. |
| 6,726,682 | B2 | 4/2004 | Harrington et al. |
| 6,773,418 | B1 | 8/2004 | Sharrow et al. |
| 7,175,634 | B2 | 2/2007 | Van Heerden |
| 7,220,259 | B2 | 5/2007 | Harrington et al. |
| 7,255,127 | B2 | 8/2007 | Davidson |
| 7,329,265 | B2 | 2/2008 | Burbank et al. |
| 7,331,923 | B2 | 2/2008 | Weichselbaum et al. |
| 7,428,904 | B2 | 9/2008 | Nikolchev et al. |
| 7,441,460 | B2 | 10/2008 | Krupa et al. |
| 7,479,145 | B2 | 1/2009 | Burbank et al. |
| 7,621,276 | B2 | 11/2009 | Tal et al. |
| 7,669,601 | B2 | 3/2010 | Tal |
| 7,678,106 | B2 | 3/2010 | Lee |
| 7,763,033 | B2 | 7/2010 | Gruber et al. |
| 7,918,795 | B2 | 4/2011 | Grossman |
| 7,931,029 | B2 | 4/2011 | McIntyre |
| 8,062,286 | B2 | 11/2011 | Shippert |
| 8,256,453 | B2 | 9/2012 | Clementi et al. |
| 8,555,727 | B2 | 10/2013 | Neatrour |
| 2002/0120265 | A1 | 8/2002 | Fowler |
| 2004/0092875 | A1 | 5/2004 | Kochamba |
| 2004/0163650 | A1 | 8/2004 | Lowe et al. |
| 2005/0209564 | A1* | 9/2005 | Bonner et al. ............ 604/173 |
| 2005/0288551 | A1 | 12/2005 | Callister et al. |
| 2005/0288664 | A1 | 12/2005 | Ford et al. |
| 2006/0212043 | A1 | 9/2006 | Grillo |
| 2007/0049951 | A1 | 3/2007 | Menn |
| 2007/0112355 | A1 | 5/2007 | Salahieh et al. |
| 2007/0156126 | A1 | 7/2007 | Flaherty |
| 2008/0033458 | A1 | 2/2008 | McLean et al. |
| 2008/0058833 | A1 | 3/2008 | Rizvi |
| 2009/0082741 | A1 | 3/2009 | Hu |
| 2009/0088725 | A1 | 4/2009 | Bataille et al. |
| 2010/0160816 | A1 | 6/2010 | Parihar et al. |
| 2010/0168514 | A1 | 7/2010 | Callister et al. |
| 2010/0198214 | A1 | 8/2010 | Layton et al. |
| 2010/0274260 | A1 | 10/2010 | D'Arpiany et al. |
| 2011/0118627 | A1 | 5/2011 | Morton et al. |
| 2011/0166508 | A1 | 7/2011 | Lyytikainen et al. |
| 2012/0330096 | A1 | 12/2012 | Stace-Naughton et al. |
| 2013/0014762 | A1 | 1/2013 | Deckman et al. |
| 2013/0023896 | A1 | 1/2013 | Quimby |
| 2013/0087042 | A1 | 4/2013 | Furuyama et al. |
| 2013/0152942 | A1 | 6/2013 | Lyytikainen et al. |
| 2014/0326249 | A1 | 11/2014 | Cappiello et al. |
| 2016/0128729 | A1 | 5/2016 | Khurana et al. |

FOREIGN PATENT DOCUMENTS

| | | |
|---|---|---|
| EP | 1679570 | 7/2008 |
| EP | 2083772 | 8/2009 |
| JP | S50/141195 | 11/1975 |
| JP | H10-507384 | 7/1998 |
| JP | H10-510444 | 10/1998 |
| WO | WO 97/22379 | 6/1997 |
| WO | WO 01/21116 | 3/2001 |
| WO | WO 2007/098618 | 9/2007 |
| WO | WO 2008/064280 | 5/2008 |
| WO | WO 2012/054466 | 4/2012 |
| WO | WO 2012/060932 | 5/2012 |
| WO | WO 2013/082452 | 6/2013 |
| WO | WO 2014/205351 | 12/2014 |

OTHER PUBLICATIONS

Written Opinion for Singapore Application No. 201302663-8, mailed Apr. 30, 2014, 9 pages.
Written Opinion for Singapore Application No. 201302663-8, mailed Dec. 22, 2014, 10 pages.
International Search Report and Written Opinion for International Application No. PCT/US2014/043417, mailed Dec. 5, 2014, 11 pages.
International Search Report and Written Opinion for International Application No. PCT/US2011/056688, mailed May 3, 2012.
International Search Report and Written Opinion for International Application No. PCT/US2012/067335, mailed Apr. 22, 2013.
Garcia, A., "Minimally Invasive Surgery," OBG Management, 21(4):22-34 (2009).
Office Action for Japanese Application No. 2013-534069, mailed Sep. 1, 2015, 2015 6 pages.
Supplementary European Search Report for European Application No. 12853787.5, mailed Jul. 24, 2015, 7 pages.
Office Action for Chinese Application No. 201180050217.8, issued Sep. 25, 2015, 17 pages.
Office Action for Chinese Application No. 201280068772.8, issued Oct. 9, 2015, 19 pages.
International Search Report and Written Opinion for International Application No. PCT/US2015/042523, mailed Oct. 27, 2015, 10 pages.
Examination Report for European Application No. 11834981.0, mailed Jan. 18, 2016.
Examination Report for European Application No. 12853787.5, mailed Apr. 4, 2016.
Second Office Action for Chinese Application No. 201280068772.8, issued May 4, 2016.
Office Action for European Application No. 11834981.0, mailed Jul. 29, 2016.

* cited by examiner

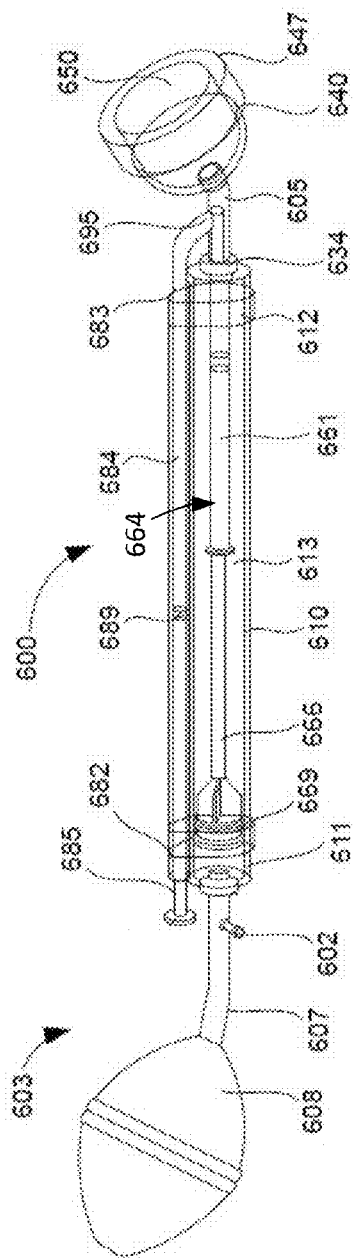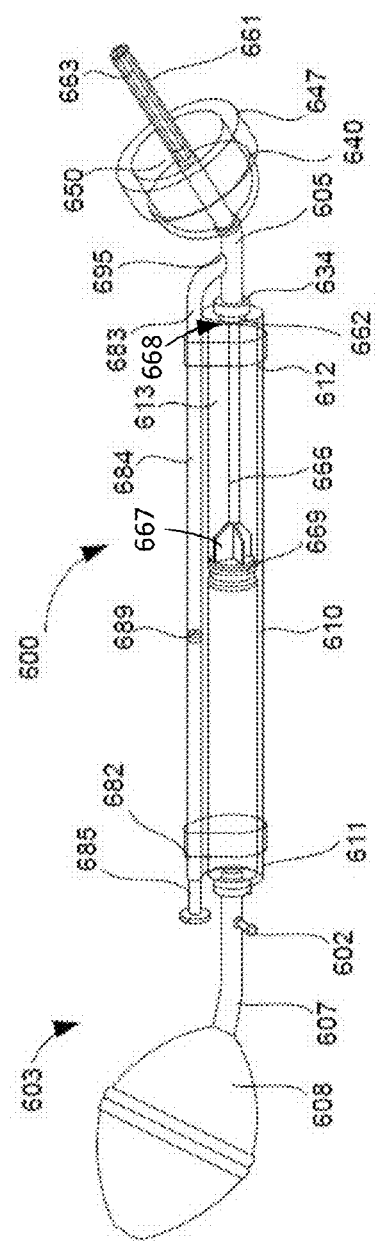

METHODS AND APPARATUS FOR INSERTING A DEVICE OR PHARMACEUTICAL INTO A BODY CAVITY

CROSS-REFERENCE TO RELATED APPLICATIONS

This application is a continuation of International Application No. PCT/US2011/056688, entitled "Methods and Apparatus for Inserting a Device or Pharmaceutical into a Body Cavity," filed Oct. 18, 2011, which claims priority U.S. Provisional Application Ser. No. 61/394,120, entitled "Methods and Apparatus for Inserting a Device or Pharmaceutical into a Body Cavity," filed Oct. 18, 2010, each of which is incorporated herein by reference in its entirety.

BACKGROUND

The embodiments described herein relate to apparatus and methods for inserting a device and/or pharmaceutical into a body cavity. More particularly, the embodiments described herein relate to apparatus and methods for inserting an intrauterine device (IUD) into the uterus.

Difficulty of insertion is a significant hurdle to the more widespread use of known IUDs by physicians and health care workers worldwide. Known methods of inserting the IUDs involve four pieces of equipment and multiple operations. In particular, known methods of IUD insertion include the use of a vaginal speculum, a cervical tenaculum, an os finder (when needed) a uterine sound, and the IUD inserter. First, a speculum is positioned to visualize the cervix. Second, the cervix is clamped with downward traction using a cervical tenaculum to substantially straighten and/or align the cervix with the uterine cavity. In certain circumstances, an os finder is used to locate and dilate the cervical os. Third, a uterine sound is used to determine the depth of the uterine cavity, which is the depth to which the IUD will be inserted. Fourth, the arms of the IUD are folded back and tucked into the tube of the inserter. Fifth, the inserter is pushed into the vagina until the health care provider can find the opening of the cervical canal, and then is inserted via the cervix into the uterus to the depth measured by the sounding process. Sixth, the tube of the inserter is pulled back to release the arms of the IUD from the tube at the fundus of the uterus. In some known procedures, the inserter tube is again pushed up against the base of the arms of the IUD to ensure highest achievable placement within the endometrial cavity. The inserter is then carefully extracted from the uterus, cervix, and vagina such that the placement of the IUD is not disrupted. Lastly, the practitioner must cut the IUD strings to ensure that a sufficient length (e.g., at least 2.5 cm) of the withdrawal string is exposed in the vagina.

The insertion of an IUD according to such known methods can often result in misplacement of the IUD and/or other complications. Said another way, known methods of IUD insertion involve a series of precise operations to ensure proper placement of the IUD. Even slight procedural deviations when using known methods and tools for IUD insertion can lead to uterine wall perforations, increased chance of embedding of the IUD in the endometrium, and/or expulsion of the IUD. In addition, it is possible to push microbes from the vagina into the uterus during the insertion process, which can lead to complications such as pelvic inflammatory disease (PID).

Thus, a need exists for improved apparatus and methods for inserting an intrauterine device (IUD) into the uterus that will reduce these risks and allow IUD insertions to be performed by health care providers across all spectra of medicine.

SUMMARY

Apparatus and methods for inserting a device and/or pharmaceutical into a body cavity are described herein. In some embodiments, an implant delivery device includes a housing, a head and an insertion member. The housing defines a housing passageway. The head, which defines a head passageway, is configured to rotate (e.g., the head can flex, rotate, pivot, etc.) relative to the housing. Collectively, the housing passageway and the head passageway define an insertion passageway such that at least a portion of the insertion passageway is nonlinear (e.g., is curved, includes nonparallel segments or the like). The insertion member has a distal end portion configured to be removably coupled to an implant. The insertion member is disposed within the housing such that, at least a portion of a proximal end of the insertion member is within the housing passageway. The insertion member is configured to bend, pivot, and/or rotate (e.g., between a proximal and distal end) within a portion of the insertion passageway to convey the implant to a target tissue.

BRIEF DESCRIPTION OF THE DRAWINGS

FIGS. 20-24 are side views of an implant delivery device according to an embodiment, in a first, second, third, fourth, and fifth configuration, respectively.

DETAILED DESCRIPTION

Figure 1:
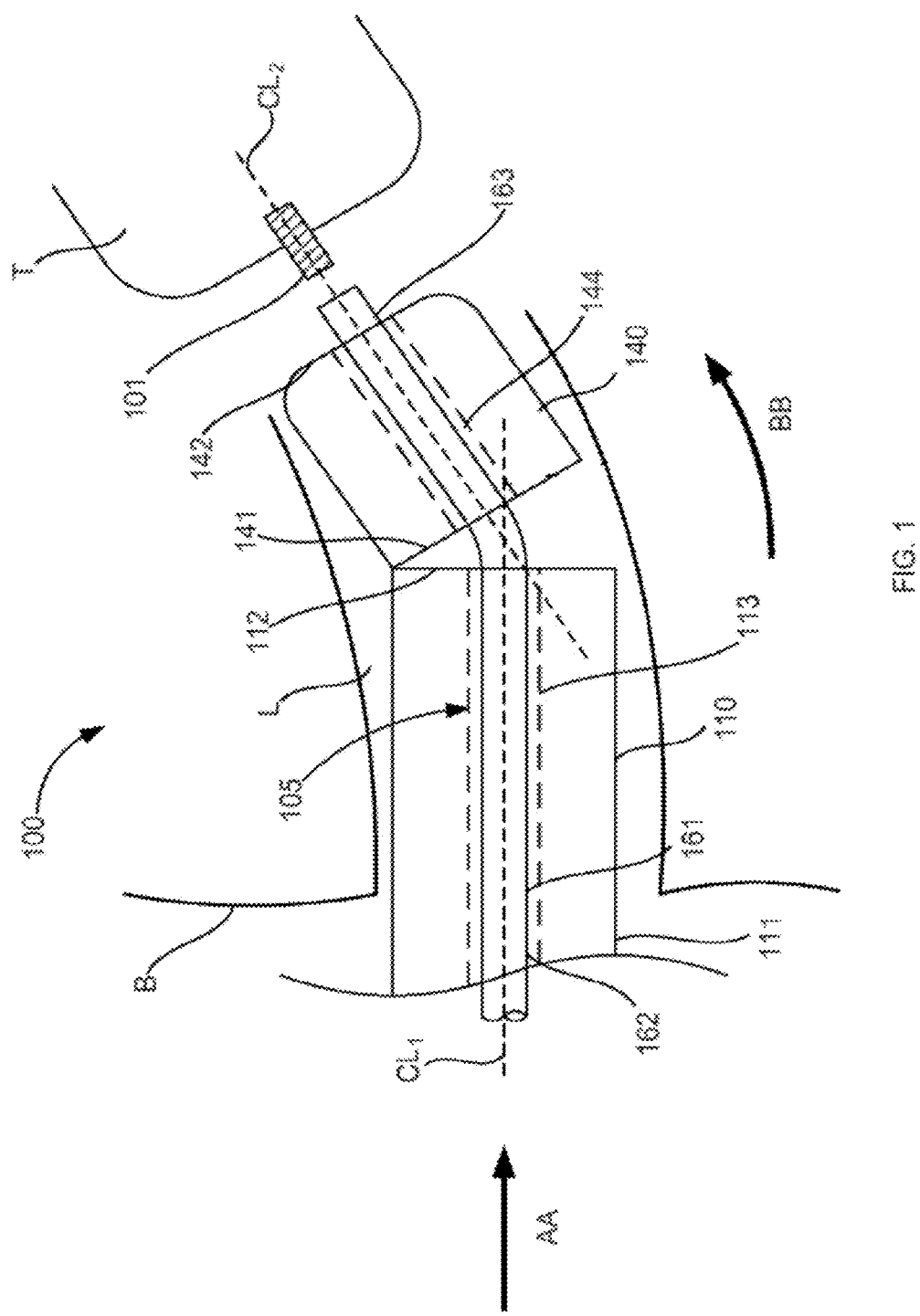
FIG. 1 is a schematic illustration of an implant delivery device according to an embodiment.

Apparatus and methods for inserting a device and/or pharmaceutical into a body cavity are described herein. In some embodiments, an implant delivery device includes a housing, a head and an insertion member. The housing defines a housing passageway. The head, which defines a head passageway, is configured to rotate (e.g., the head can flex, rotate, pivot, etc.) relative to the housing. Collectively, the housing passageway and the head passageway define an insertion passageway such that at least a portion of the insertion passageway is nonlinear (e.g., is curved, includes nonparallel segments or the like). The insertion member has a distal end portion configured to be removably coupled to an implant. The insertion member is disposed within the housing such that, at least a portion of a proximal end of the insertion member is within the housing passageway. The insertion member is configured to bend, pivot, and/or rotate (e.g., between a proximal and distal end) within a portion of the insertion passageway to convey the implant to a target tissue.

In some embodiments, an implant delivery device includes a housing, a first insertion member, a second insertion member and a control member. The housing defines a housing passageway, and includes a contact portion that is configured to contact a surface associated with a target tissue, such as for example, an outer surface of a uterus and/or cervix. The first insertion member has a distal end portion configured to be removably coupled to an implant. The first insertion member includes a proximal end portion that is at least partially disposed within the housing passageway and, as such, the first insertion member can be configured to move, relative to the housing, between a first position and a second position. While in the second position, the distal end of the first insertion member is spaced apart from the contact portion of the housing by a predetermined distance. The second insertion member is coupled to the first insertion member, and is configured to move relative to the first insertion member to decouple (i.e., remove from contact) the implant from the distal end portion of the first insertion member. The implant delivery device further includes a control mechanism (e.g., valve, clutch, brake, ratchet, and/or the like) configured to limit the implant force exerted by the second insertion member on the implant when the second insertion member moves to decouple the implant from the first insertion member.

In some embodiments, an implant delivery device includes a housing defining a housing passageway. The housing includes a contact portion that is configured to contact a surface associated with a target tissue. The implant delivery device includes at least one insertion member, having a distal end portion configured to be removably coupled to an implant. The insertion member includes a proximal end portion that is at least partially disposed within the housing passageway. The implant delivery device further includes an energy storage member, such as, for example, a compressed gas container, a biasing member (e.g., a spring), or the like, operably coupled to the housing. The energy storage member is configured to produce a force, when actuated, to move the insertion member relative to the housing, between a first position and a second position to convey the implant to the target tissue.

In some embodiments, an implant delivery device includes a housing defining a housing passageway. The housing includes a contact portion configured to contact a surface associated with a target tissue. The contact portion includes a sidewall and defines a volume. The contact portion is configured to substantially circumscribe a bodily cavity associated with the target location. For example, in some embodiments, the contact portion is configured to substantially surround a cervical opening and/or a cervical canal. The volume is configured to partially circumscribe the body cavity associated with the target tissue. In this manner, the sidewall of the contact portion and a portion of the surface associated with the target tissue collectively enclose the volume defined by the contact portion. The housing further includes a vacuum channel in fluid communication with the volume defined by the contact portion and that is operably coupled to a vacuum source. The vacuum source, when actuated, produces a vacuum within the volume such that a vacuum force is exerted on the portion of the surface. The implant delivery device includes at least one insertion member, having a distal end portion configured to be removably coupled to an implant. The insertion member includes a proximal end portion that is at least partially disposed within the housing. The insertion member is configured to move, relative to the housing, between a first position and a second position to convey the implant to the target tissue via the body cavity.

In some embodiments, a method includes inserting a contact portion of an implant delivery device into a body in a distal direction until the contact portion contacts an outer surface of a cervix of a uterus. The method further includes producing a vacuum within a volume defined by the contact portion of the implant delivery device such that a suction force is applied to at least a portion of the outer surface of the cervix. With the suction force applied to the outer surface, the implant delivery device is moved in a proximal direction to substantially align a uterine cavity and a cervical canal. More particularly, the implant delivery device is moved proximally until an angle between the uterine cavity and the cervical canal is greater than approximately 90 degrees. In some embodiments, the implant delivery device is moved proximally until the angle between the uterine cavity and the cervical canal is such that a desired level of alignment and/or "straightness" is achieved. For example, in some embodiments, the implant delivery device is moved proximally until the angle between the uterine cavity and the cervical canal is greater than approximately 115 degrees, 135 degrees or 165 degrees. The method further includes moving an insertion member within a passageway defined by the implant delivery device until a distal end portion of the insertion member is disposed within the uterine cavity.

In some embodiments, a method includes inserting a housing of an implant delivery device into a body until a contact portion of the housing contacts an outer surface of a cervix of a uterus. The implant delivery device includes an implant removably coupled to a distal end of a first insertion member. The method includes moving the first insertion member, relative to the housing, such that the distal end portion is disposed within a cervical canal defined by the cervix. In some embodiments, the first insertion member is configured to be moved a predetermined distance (e.g., a minimum anatomical depth associated with the uterus). The method further includes moving a second insertion member, relative to the first insertion member, to decouple the implant from the first insertion member. In some embodiments, the force exerted by the second insertion member to decouple the implant from the first insertion member is maintained below a predetermined threshold.

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

The term "parallel" is used herein to describe a relationship between two geometric constructions (e.g., two lines, two planes, a line and a plane or the like) in which the two geometric constructions are substantially non-intersecting as they extend substantially to infinity. For example, as used herein, a line is said to be parallel to another line when the lines do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

FIG. 1 is a schematic illustration of an implant delivery device 100 according to an embodiment. The implant delivery device 100 includes a housing 110, a head 140 and an insertion member 161. The housing includes a proximal end portion 111 and a distal end portion 112, and defines a housing passageway 113 therebetween. The housing passageway 113 defines a first centerline $CL_1$ between the proximal end 111 and the distal end 112. The housing 110 can be any suitable shape, size, or configuration. For example, the housing 110 can be substantially cylindrical with a diameter suitable for insertion into a body orifice.

The distal end portion 112 of the housing 110 is coupled to a proximal end 141 of the head 140 such that the head 140 can flex, rotate and/or pivot relative to the housing 110, as shown in FIG. 1 by arrow BB. The head 140 can be coupled to the housing via any suitable mechanism. For example, the distal end 112 of the housing 110 can include a set of apertures (not shown in FIG. 1) and the head 140 can include a set of protrusions (not shown in FIG. 1). The apertures can be configured to receive the protrusions to pivotally couple the head 140 to the housing 110. Similarly stated, the protrusions included in the head 140 can define an axis about which the head 140 can pivot relative to the housing 110. In other embodiments, the head 140 can be coupled to the housing 110 via a flexible sleeve (not shown in FIG. 1) configured to receive the distal end portion 112 of the housing 110 and a proximal end 141 of the head 140. In this manner, the sleeve can flexibly couple the head 140 to the housing 110 such that the head 140 can rotate relative to the housing 110 with one or more degrees of freedom. Although the head 140 is shown as being directly coupled to the housing 110 (i.e., without any intervening structure), in some embodiments the head 140 can be coupled to the housing 110 via intervening structure. Similarly stated, in some embodiments the head 140 can be coupled to the housing 110 without the head 140 being in direct physical contact with the housing 110.

The head 140 includes the proximal end 141 and a distal end 142 and defines a head passageway 144 therebetween. The head passageway 144 defines a second centerline $CL_2$ between the proximal end 141 and the distal end 142. The housing passageway 113 and the head passageway 144 collectively define an insertion passageway 105 such that, at least a portion of the insertion passageway 105 is nonlinear. Similarly stated, the head 140 is configured to rotate relative to the housing 110 such that the second centerline $CL_2$ defined by the head passageway 144 is nonparallel to the first centerline $CL_1$ defined by the housing passageway 113. Said another way, the head 140 is configured to rotate relative to the housing 110 such that the second centerline $CL_2$ is angularly offset from the first centerline $CL_1$. In this manner, the insertion passageway 105 includes a bend and/or curve such that the insertion passageway 105 does not define a straight line. As described in more detail herein, this configuration allows the insertion member 161 to be inserted into curved and/or nonlinear bodily lumen L while minimizing patient discomfort associated with straightening the bodily lumen.

The insertion member 161 has a proximal end 162 and a distal end 163. The insertion member 161 can be any suitable shape, size, or configuration. For example, in some embodiments, the insertion member 161 can define a lumen (not shown in FIG. 1). In some embodiments, the insertion member 161 can be substantially solid (i.e., the insertion member 161 does not define a lumen). The insertion member 161 can be formed from any suitable material. For example, in some embodiments, the insertion member 161 can be formed from a flexible material such as a rubber, elastomer, and/or plastic.

The insertion member 161 is at least partially disposed within the insertion passageway 105. Said a different way, at least a portion of the proximal end 162 of the insertion member 161 is disposed within the housing passageway 113. At least a portion of the insertion member 161 can move within the insertion passageway 105. In some embodiments, the insertion member 161 can bend, pivot, and/or rotate as the insertion member 161 moves within a portion of the insertion passageway 105.

The distal end 163 of the insertion member 161 is configured to be removably coupled to an implant 101. In some embodiments, the implant 101 is an intrauterine device (IUD) configured to be implanted into a target portion of a uterus of a patient. In other embodiments, the implant 101 can be a pharmaceutical and or other medical device configured to be placed at a target location within a body of a patient.

In use, the implant delivery device 100 is inserted into a bodily lumen L defined by a portion of a body B of a patient, as shown in FIG. 1 by arrow AA. In some embodiments, the bodily lumen L is substantially nonlinear (e.g., the bodily lumen L can have a curved portion). As described above, the head 140 can be moved relative to the housing 110 such that the insertion passageway 105 is substantially nonlinear. The head 140 can be rotated relative to the housing 110 either before during or after the insertion. In this manner, the distal end 163 of the head 161 can be aligned with, placed into contact with and/or engage a surface of the target tissue T. At least a portion the insertion member 161 can be moved within the insertion passageway 105, such that the distal end 163 of the insertion member 161 extends beyond the distal end 142 of the head 140 to deliver the implant 101 to a target tissue T. As described above, a portion of the insertion member 161 bends when the insertion member 161 is moved within the portion of the insertion passageway 105.

In some embodiments, for example, the implant delivery device 100 can be inserted into a vagina of a patient in a distal direction. Similarly stated, the implant delivery device 101 can be moved within the vagina toward a cervix of a uterus. In some embodiments, the head 140 can contact a portion of the cervix. With the head 140 of the implant delivery device, in contact with and/or near an outer surface of the cervix, the insertion member 161 can be moved distally within the insertion passageway 105. As the insertion member 161 is advanced in the distal direction, the insertion member 161 can bend, rotate, and/or conform to the bend and/or curve in the insertion passageway 105. The distal end 163 of the insertion member 161 can be configured to extend beyond the distal end 142 of the head 140 and into (or through) a cervical os (i.e., the opening of a uterine cavity). With the insertion member 161 inserted into the uterine cavity, the insertion member 161 can deliver the implant 101 to a fundus of the uterus (i.e., a portion of the uterus opposite the cervical os). In some embodiments, the implant delivery device 100 can include a control member (not shown in FIG. 1) that limits the force exerted by the insertion member 161 on the implant 101 (and/or the fundus of the uterus) as it moves in a distal direction. In some embodiments, the implant delivery device 100 can include a mechanism (not shown in FIG. 1) that limits the distance through which the distal end 163 of the insertion member 161 extends beyond the distal end 142 of the head 140 during the insertion process.

Figure 2:
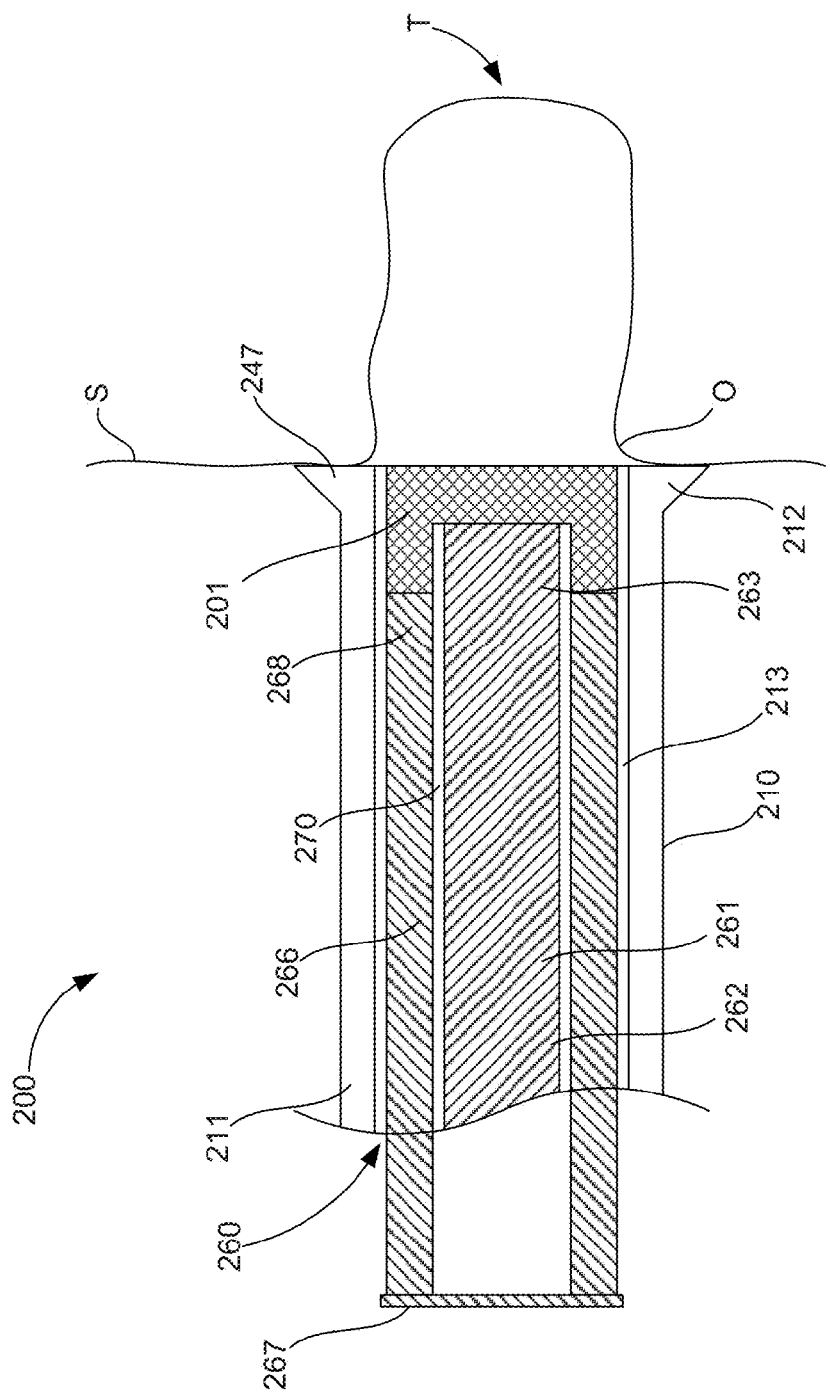
FIGS. 2-4 are schematic illustrations of an implant delivery device according to an embodiment, in a first, second, and third configuration, respectively.
Figure 3:
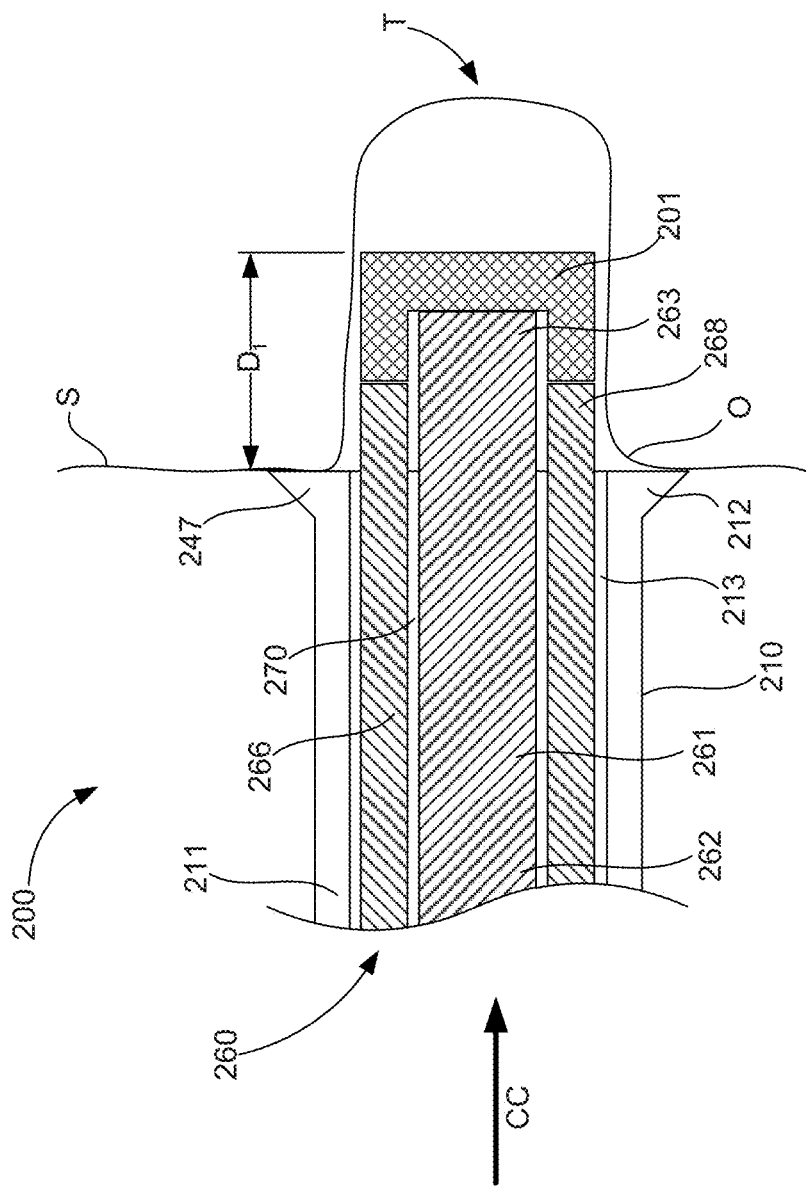
Figure 4:
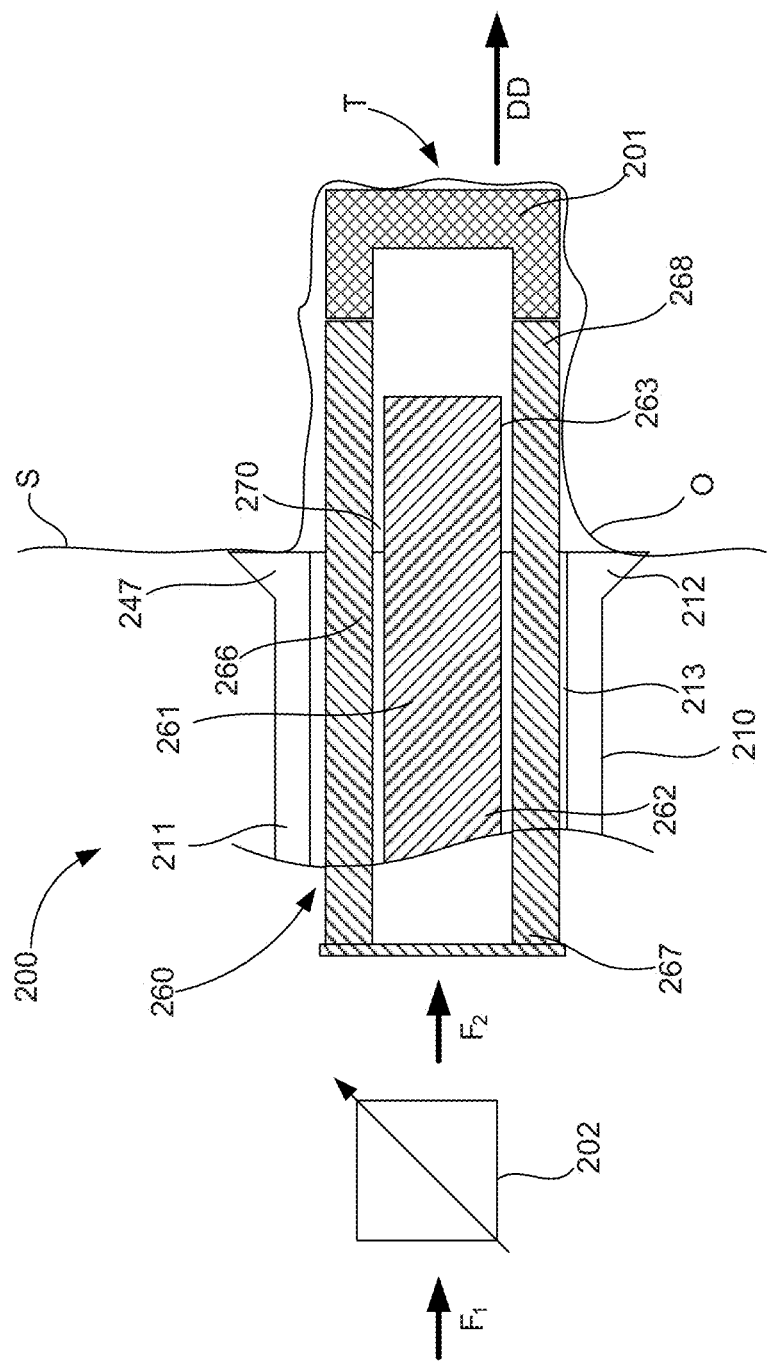

FIGS. 2-4 are schematic illustrations of an implant delivery device 200 according to another embodiment, in a first, a second, and a third configuration, respectively. The implant delivery device 200 includes a housing 210, an insertion assembly 260 and a control mechanism 202 (see FIG. 4). The housing 210 includes a proximal end 211 and a distal end 212, and defines a housing passageway 213 therebetween. The distal end 212 of the housing 210 includes a contact portion 247 that is configured to contact a surface S associated with a target tissue T. The surface S can be any suitable surface, such as an external surface (e.g., skin) or an internal surface (e.g., an outer surface of the cervix). The housing 210 can be any suitable shape, size, or configuration. For example, the housing 210 can be substantially cylindrical with a diameter suitable for insertion into a body orifice. In some embodiments, the housing 210 is formed from a flexible material such as a rubber, elastomer, and/or plastic. In some embodiments, the housing 210 can include a set of components that are rotatably coupled together. For example, the housing 210 can include a head portion that is rotatably coupled to the housing 210, similar to the arrangement of the head 140 shown and described above.

The insertion assembly 260 includes a first insertion member 261 and a second insertion member 266. As described in more detail below, at least a portion of the insertion assembly 260 is configured to move relative to the housing 210 within the housing passageway 213. The first insertion member 261 includes a proximal end portion 262 and a distal end portion 263. The proximal end portion 262 is at least partially disposed within the housing passageway 213. The distal end portion 263 is configured to be removably coupled to an implant 201. In some embodiments, the implant 201 is an intrauterine device (IUD) configured to be implanted into a target portion of a uterus of a patient. In other embodiments, the implant 201 can be a pharmaceutical and or other medical device configured to be placed at a target location within a body of a patient.

The first insertion member 261 can be any suitable shape, size, or configuration, and can include any suitable feature for removably coupling the implant 201 thereto. For example, in some embodiments, distal end portion 263 of the first insertion member 261 can include a protrusion and/or opening (not shown in FIGS. 2-4) configured to be matingly coupled to a corresponding protrusion and/or opening of the implant 201. In other embodiments, the first insertion member 261 can define a lumen (not shown in FIGS. 2-4) within which at least a portion of the implant 201 can be disposed. In yet other embodiments, the distal end portion 263 can include a snap fit joint, threaded fitting, or the like configured to removably couple the implant 201 thereto. Additionally, the insertion member 261 can be formed from any suitable material. For example, in some embodiments, the first insertion member 261 can be formed from a flexible material such as a rubber, elastomer, polymer, and/or plastic.

The second insertion member 266 includes a proximal end portion 267 and a distal end portion 268. The second insertion member 266 is movably coupled to the first insertion member 261. Specifically, the second insertion member 266 defines an insertion channel 270 between the proximal end portion 267 and the distal end 268 within which at least a portion of the first insertion member 261 is disposed. In this manner, as described below, the second insertion member 266 can move about the first insertion member 261 to decouple the implant 201 from the distal end portion 263 of the first insertion member 261. Although the second insertion member 266 is shown as defining a channel 270 and being disposed about the first insertion member 261, in other embodiments, the second insertion member 266 can be coupled to the first insertion member 261 in any suitable configuration. For example, in some embodiments, the second insertion member 266 can be disposed within the first insertion member 261. In other embodiments, the second insertion member 266 can be disposed beside the first insertion member 261.

In use, the implant delivery device 200 can be moved between several different configurations to deliver the implant 201 to the target tissue T. In the first configuration, as shown in FIG. 2, the contact portion 247 is in contact with the surface S associated with a target tissue T. The distal end portion 263 of the first insertion member 261 and the distal end portion 268 of the second insertion member 266 are each disposed within the housing passageway 213 at the distal end portion 212 of the housing 210 such that the distal end of the implant 201 is substantially flush with the contact portion 247. In other embodiments, the first insertion member 261 and the second insertion member 266 can be disposed within the housing passageway 213 such that the distal end of the implant 201 is spaced apart from the contact portion 247 in the proximal direction (i.e., recessed within the distal end portion 212) or in the distal direction (i.e., protruding from the distal end portion 212).

To move the device 200 from the first configuration (FIG. 2) to the second configuration (FIG. 3), a force is applied to advance the insertion assembly 260 in a distal direction, as shown in FIG. 3 by the arrow CC. In this manner, the first insertion member 261 and the second insertion member 266 move relative to the housing 210 and advance through an opening O defined by the contact surface S of the target tissue T. More specifically, the first insertion member 261 is configured to advance a predetermined distance $D_1$ beyond the contact portion 247 of the housing 210. In some embodiments, the housing 210 can include an engagement portion (not shown in FIGS. 2-4) or other mechanism to limit the distance the first insertion member 261 extends beyond the contact portion 247 when the implant delivery device 200 is in the second configuration. For example, in some embodiments, the first insertion member 261 can be configured to extend approximately 5 cm beyond the contact portion 247. In other embodiments, the first insertion member 261 can extend approximately 7 cm beyond the contact portion 247. In some embodiments, the distance $D_1$ can be associated with an anatomical feature related to the target tissue T. For example, in some embodiments, the distance $D_1$ can be a minimum depth of the uterus for which insertion of an IUD is recommended.

To move the implant delivery device 200 from the second configuration (FIG. 3) to the third configuration (FIG. 4), a force $F_2$ is applied to at least the second insertion member 266. Thus, the second insertion member 266 is moved relative to the first insertion member 261 in the distal direction toward the target tissue T, as shown in FIG. 4 by arrow DD. When the second insertion member 266 moves relative to the first insertion member 261, it decouples the implant 201 from the first insertion member 261. In this manner, the implant 201 is placed in contact with and/or adjacent the target tissue T.

The control mechanism 202 configured to maintain, reduce, regulate and/or otherwise limit the force $F_2$ exerted on the second insertion member 266 and/or exerted by the second insertion member 266 on the implant 266. In this manner, the implant 201 can be delivered to the target tissue T with an amount of force that minimizes the potential damage to the target tissue T and/or patient discomfort. The control mechanism 202 can be any suitable mechanism, such as, for example, a valve, a clutch, a ratchet mechanism, and/or the like. In particular, the control mechanism 202 can be configured to receive a first force $F_1$ and transmit at least a portion of the force $F_1$ to the first insertion member 261 and/or the second insertion member 266. When the force exerted on the second insertion member 266 increases to a threshold level, the control mechanism 202 can limit the magnitude of the force $F_2$ transmitted to the first insertion member 261 and/or the second insertion member 266. Therefore, in use, the control mechanism 202 can regulate the force and/or pressure exerted on the second insertion member 266 by reducing the first force $F_1$ transmitted through the control mechanism 202 to a second force $F_2$ that is less than the first force $F_1$.

The force applied to the insertion assembly 260, the first insertion member 261 and/or the second insertion member 266 (e.g., the force F1 and/or the force F2) can be produced in any suitable manner. For example, in some embodiments, the force can be produced manually (e.g., by action of the user). For example, in some embodiments, the force can be produced manually when the user applies a force (e.g., squeezes) a lever (not shown in FIGS. 2-4) coupled to the insertion assembly 260. In other embodiments, the force can be produced manually when the user manually pressurized a fluid in communication with the insertion assembly 260. In yet other embodiments, the force can be produced by an energy storage member (not shown in FIGS. 2-4). In some embodiments, the force can be produced via a biasing member (e.g., a spring system, a resilient polymer, or the like), an electrical energy storage member, and/or a magnetic member. In other embodiments, the force can be applied via a pneumatic or hydraulic system operably coupled to the housing passageway 213.

Figure 5:
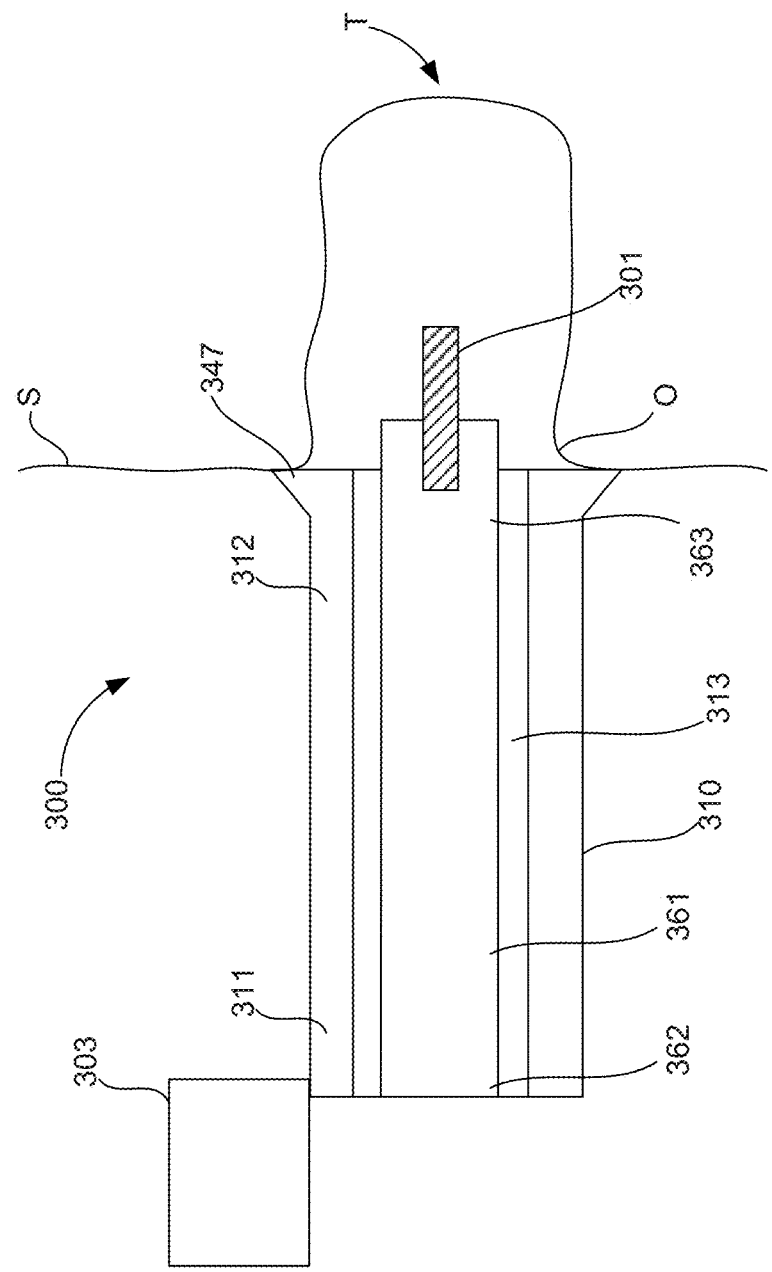
FIGS. 5 and 6 are schematic illustrations of an implant delivery device according to an embodiment, in a first and second configuration, respectively.
Figure 6:
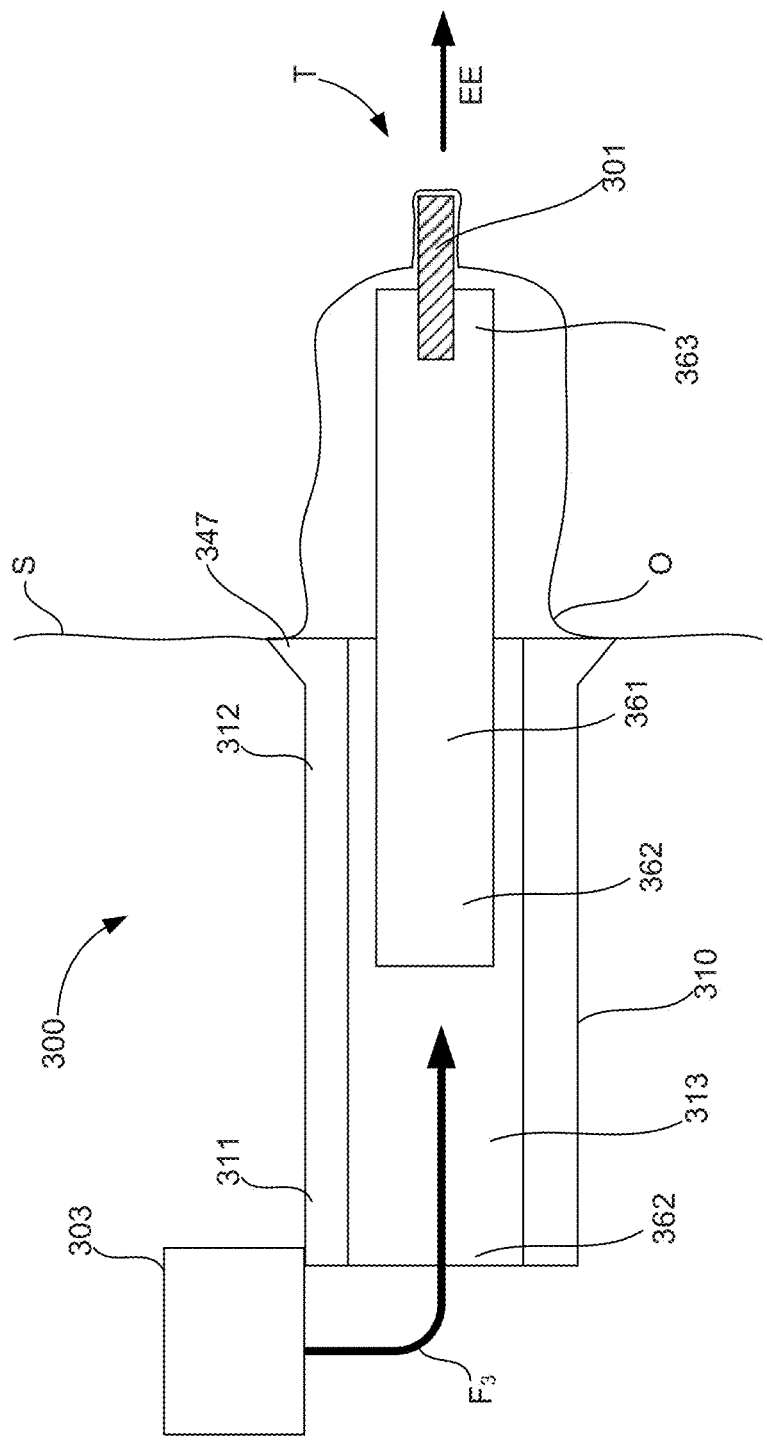

FIGS. 5 and 6 are schematic illustrations of an implant delivery device 300 according to an embodiment that includes an energy storage member 303 to produce an insertion force. The implant delivery device 300 includes a housing 310, an insertion member 361 and the energy storage member 303. The housing 310 includes a proximal end portion 311 and a distal end portion 312, and defines a housing passageway 313. The distal end portion 312 of the housing 310 includes a contact portion 347 configured to contact a surface S associated with a target tissue T. The surface S can be any suitable surface, such as an external surface (e.g., skin) or an internal surface (e.g., an outer surface of the cervix). The housing 310 can be any suitable shape, size, or configuration. For example, the housing 310 can be substantially cylindrical with a diameter suitable for insertion into a body orifice. In some embodiments, the housing 310 is formed from a flexible material such as a rubber, elastomer, and/or plastic. In some embodiments, the housing 310 can include a set of components that are rotatably coupled together. For example, the housing 310 is configured such that the contact portion 347 is rotatably coupled to the housing 310 via a sleeve and/or the like (not shown in FIGS. 5 and 6). In such embodiments, the housing passageway 313 can be substantially nonlinear, such that at least a portion of the housing passageway 313 bends and/or curves.

The insertion member 361 has a proximal end portion 362 and a distal end portion 363. The distal end 363 of the insertion member 361 is configured to be removably coupled to an implant 301. In some embodiments, the implant 301 is an intrauterine device (IUD) configured to be implanted into a target portion of a uterus of a patient. In other embodiments, the implant 301 can be a pharmaceutical and or other medical device configured to be placed at a target location within a body of a patient.

The insertion member 361 can be any suitable shape, size, or configuration, and can include any suitable feature for removably coupling the implant 301 thereto. For example, in some embodiments, distal end portion 363 of the insertion member 361 can include a protrusion and/or opening (not shown in FIGS. 5 and 6) configured to be matingly coupled to a corresponding protrusion and/or opening of the implant 301. In other embodiments, the insertion member 361 can define a lumen (not shown in FIGS. 5 and 6) within which at least a portion of the implant 301 can be disposed. In yet other embodiments, the distal end portion 363 can include a snap fit joint, threaded fitting, or the like configured to removably couple the implant 301 thereto. Additionally, the insertion member 361 can be formed from any suitable material. For example, in some embodiments, the insertion member 361 can be formed from a flexible material such as a rubber, elastomer, polymer, and/or plastic.

The insertion member 361 is configured to be disposed within the housing passageway 313 such that, at least a portion of the proximal end portion 362 is disposed within the housing 310. Said a different way, at least a portion of the proximal end portion 362 of the insertion member 361 is disposed within the housing passageway 313. In addition, at least a portion of the insertion member 361 is configured to move within the housing passageway 313 to convey the implant 301 to the target location T. In some embodiments, the insertion member 361 can bend, pivot, and/or rotate as the insertion member 361 moves within a portion of the housing passageway 313.

The energy storage member 303 configured to apply a force to the insertion member 361 to move the insertion member 361 between a first configuration (FIG. 5) and a second configuration (FIG. 6). As shown in FIG. 6, a force $F_3$ is applied by the energy storage member 303 to advance the insertion member 361 in a distal direction, as shown by the arrow EE. In this manner, the implant 301 can be conveyed to the target location T without the need for the user to manually produce the force $F_3$ during the delivery operation.

In some embodiments, the energy storage member 303 can be a biasing member (e.g., a spring, resilient member or the like), an electrical energy storage member, a hydraulic system, and/or a magnetic member. In other embodiments, the energy storage member 303 can be a pneumatic system operably coupled to the housing passageway 313. In some such embodiments, the pneumatic system can be controlled via a valve system including a push button activation, to produce a pressurized fluid flow that contacts the insertion member 361. In other embodiments, the pneumatic system can include an air bladder configured to be manually pressurized by the physician prior to the delivery operation, to produce a pressurized fluid flow that is stored for later use during the delivery operation. The pressurized fluid included in a pneumatic or hydraulic energy storage system can flow within a portion of the housing passageway 313, and can apply a force to a plunger (not shown in FIGS. 5 and 6) included in the insertion member 361.

In use, when the force $F_3$ is applied, the insertion member 361 moves relative to the housing 310 and advances through an opening O defined by the contact surface S of the target tissue T. In some embodiments, the insertion member 361 can be configured to advance a predetermined distance beyond the contact portion 347 of the housing 310, as described above with respect to FIGS. 2-4. In some such embodiments, the housing 310 can include an engagement portion that can limit the distance the insertion member 361 extends beyond the contact portion 347. For example, the first insertion member 361 can be configured to extend 5 cm beyond the contact portion 347.

In some embodiments, the implant delivery device 300 can include a control mechanism (not shown in FIGS. 5 and 6) configured to maintain, reduce, regulate and/or otherwise limit the force $F_3$ exerted on the insertion member 361 and/or the magnitude of the force exerted by the insertion member 361 on the implant 301. The control mechanism can be any suitable mechanism, such as, for example, a valve, a clutch, a ratchet mechanism, and/or the like and can function similarly to the control mechanism described with respect to FIGS. 2-4.

Figure 7:
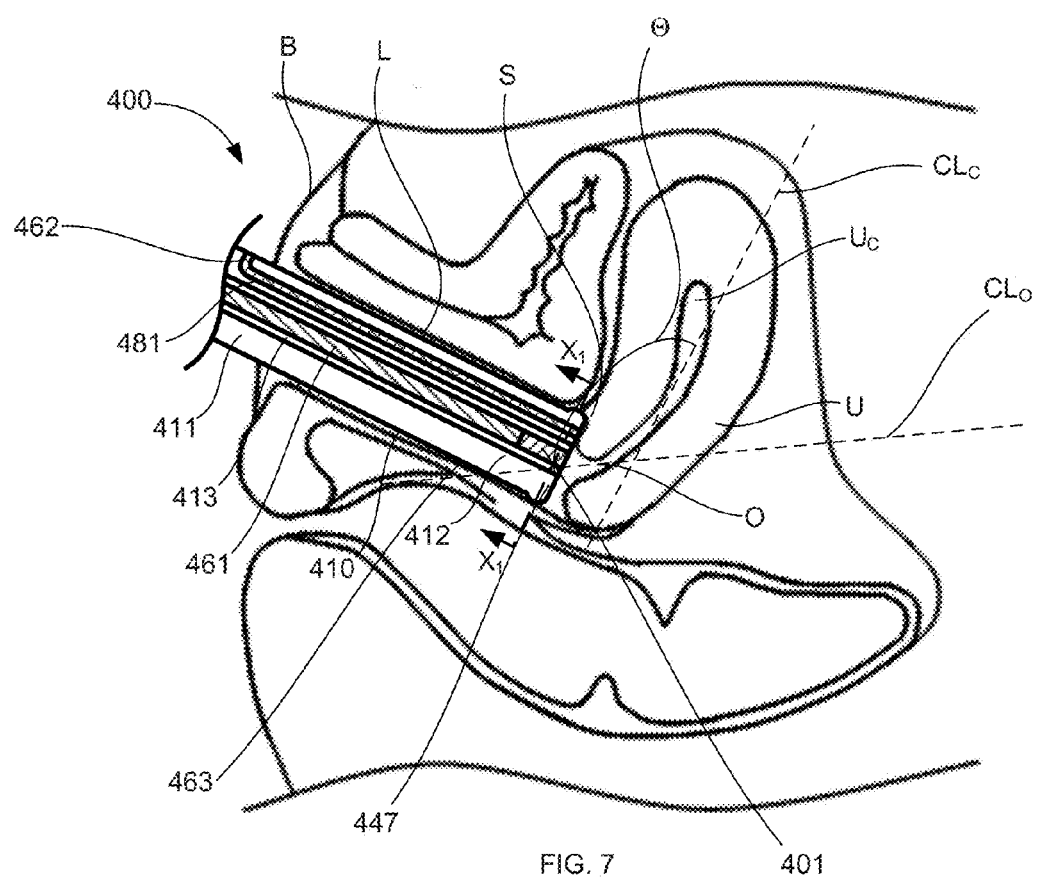
FIG. 7 is a schematic illustration of an implant delivery device according to an embodiment, in use within a body cavity, in a first configuration.
Figure 8:
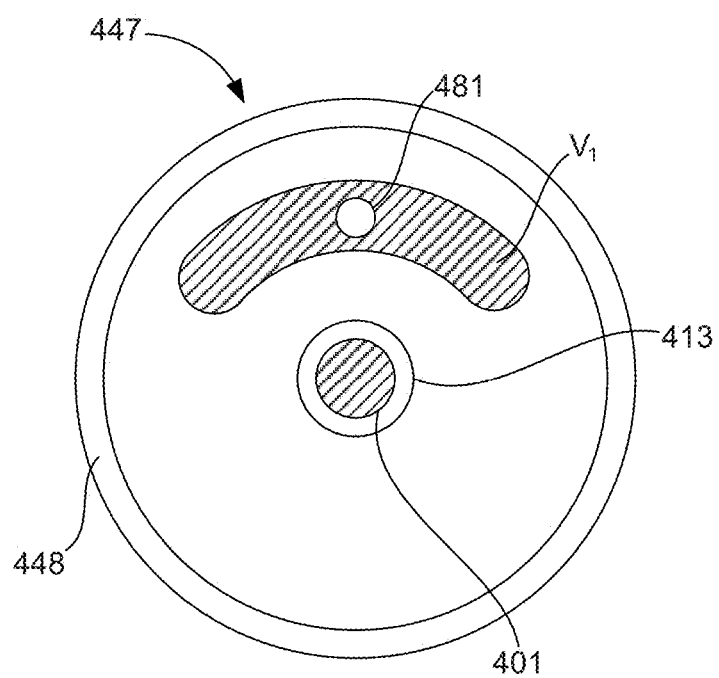
FIG. 8 is a cross-sectional view of a contact portion included in the implant delivery device of FIG. 7, taken along line $X_1$-$X_1$ in FIG. 7.
Figure 9:
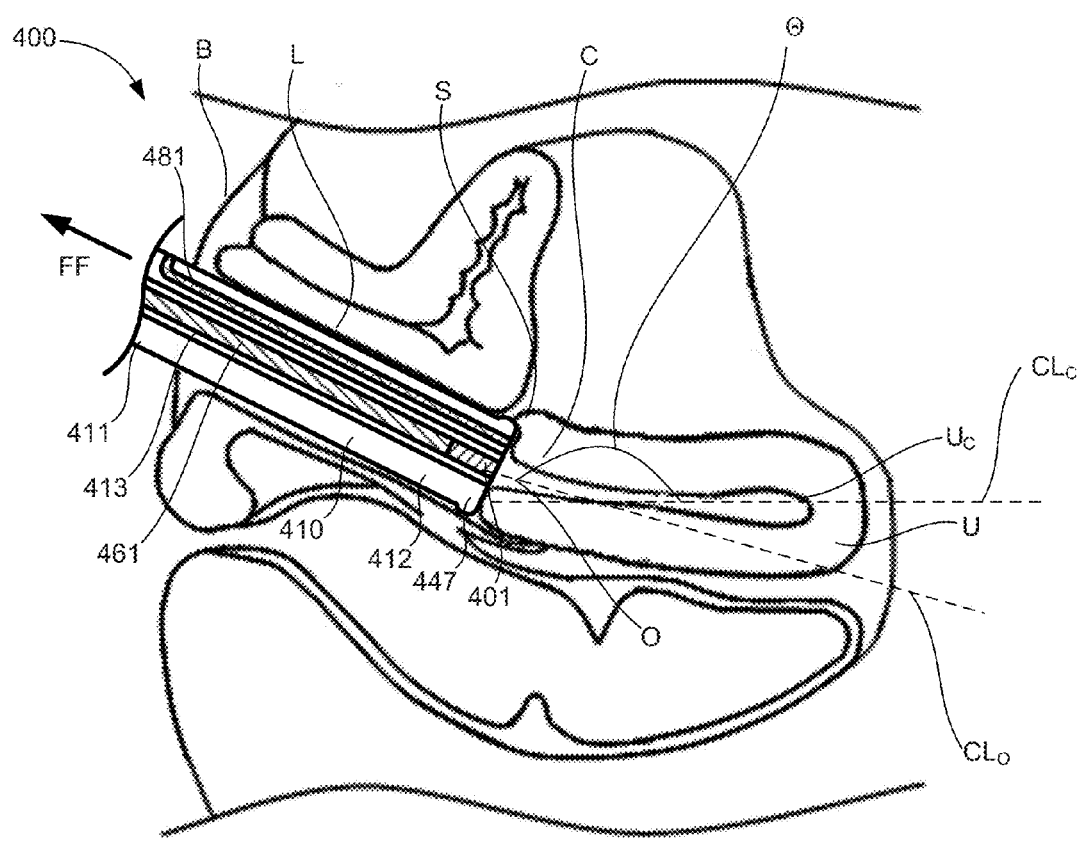
FIG. 9 is a schematic illustration of the implant delivery device of FIG. 7, in use within a body cavity.

Any of the implant delivery devices shown and described herein can be used to deliver an IUD into a uterus. In some embodiments, an implant delivery device can be configured to straighten, align and/or manipulate the uterus and/or cervix to facilitate the delivery of the IUD. For example, FIGS. 7-9 are schematic illustrations of an implant delivery device 400 according to an embodiment. The implant delivery device 400 includes a housing 410 and an insertion member 461. The housing has a proximal end portion 411 and a distal end portion 412, and defines a housing passageway 413. The housing 410 also defines a vacuum channel 481. The distal end portion 412 of the housing 410 includes a contact portion 447 configured to contact an outer surface S of the cervix C of a uterus U. The contact portion 447 includes a sidewall 448 (see FIG. 8) that defines a volume $V_1$.

The vacuum channel 481 defined by the housing 410 is in fluid communication with at least a portion of the first volume $V_1$. The proximal end of the vacuum channel 481 can be coupled to a vacuum source (not shown in FIGS. 7-9). In this manner, as described below, a vacuum can be produced within the first volume $V_1$. In some embodiments, the vacuum source can be defined by a chamber defined by the housing that includes an actuator that is manually actuated to produce a vacuum. In such embodiments, the actuator can include a plunger configured to form an airtight seal with the inner surface of the chamber. Therefore, in use, the actuator can be retracted (e.g., moved in a proximal direction) to produce a vacuum force.

The housing 410 can be any suitable shape, size, or configuration. For example, the housing 410 can be substantially cylindrical with a diameter suitable for insertion into a body orifice. In some embodiments, the housing 410 is formed from a flexible material such as a rubber, elastomer, and/or plastic. In some embodiments, the housing 410 is configured such that the contact portion 447 is rotatably coupled to the remainder of housing 410 via a sleeve, a pinned joint, a u-joint a ball joint and/or the like (not shown in FIGS. 7-9). In some such embodiments, the housing passageway 413 can be substantially nonlinear, such that at least a portion of the housing passageway 413 bends and/or curves.

The insertion member 461 has a proximal end portion 462 and a distal end portion 463. The distal end 463 portion of the insertion member 461 is configured to be removably coupled to an implant 401, such as an intrauterine device (IUD) configured to be implanted into the uterus U of a patient. In other embodiments, the implant 401 can be a pharmaceutical and or other medical device configured to be placed at a target location within a body of a patient. The insertion member 461 can be any suitable shape, size, or configuration, as described herein.

The insertion member 461 is disposed within the housing passageway 413 such that, at least a portion of the proximal end 462 is disposed within the housing 410. Said a different way, at least a portion of the proximal end 462 of the insertion member 461 is disposed within the housing passageway 413. In addition, at least a portion of the insertion member 461 is be configured to move within the housing passageway 413 to convey the implant 401 to the uterus U as described below. In some embodiments, the insertion member 461 can bend, pivot, and/or rotate before, during and/or after the insertion member 461 moves within a portion of the housing passageway 413.

As shown in FIG. 7, in use the implant delivery device 400 can be inserted into a bodily lumen L defined by the body B of a patient, such as, for example, the lumen L defined by the inner walls of the vagina. The implant delivery device 400 can be inserted into the lumen L until at least a portion of the contact portion 447 contacts and/or engages the outer surface S of a cervix C of the uterus U. More specifically, the contact portion 447 is configured to contact the outer surface S of the cervix C and substantially circumscribe a cervical opening O defined by the cervix C. Similarly stated, when the contact portion 447 is positioned against of the cervix C, the sidewall 448 substantially surrounds the cervical opening O. In this manner, the distal end portion 463 and/or the implant 401 can be substantially aligned with the cervical opening O to facilitate delivery of the implant into the uterus U.

When the implant delivery device 400 is positioned as shown in FIG. 7, the first volume $V_1$ partially circumscribes the cervical opening O. For example, in some embodiments, the contact portion 447 can be configured such that the volume $V_1$ is disposed adjacent the anterior portion of the outer surface S of the cervix C. Moreover, when the contact portion 447 is positioned against the outer surface S of the cervix C a portion of the outer surface S and the side wall 448 substantially enclose the first volume $V_1$. In this manner, when the vacuum source is actuated, a vacuum is produced within the first volume $V_1$, thereby resulting in the exertion of a suction force on the portion of the outer surface S of the cervix C.

When the vacuum source is actuated and the suction force is applied to the contact surface S of the cervix C, the implant delivery device 400 can be used to substantially align, straighten and/or reposition the uterine cavity $U_C$ and the opening O to facilitate insertion of the implant 401. Similarly stated, when the suction force is applied to the contact surface S of the cervix C a cervical canal, the implant delivery device 400 can be used to place the uterus U of the patient in more suitable position to receive the implant 401. More particularly, as shown in FIG. 9, with the vacuum source exerting a suction force on the portion of the contact surface S of the cervix C, the implant delivery device 400 can be moved in a proximal direction, as shown in FIG. 9 by arrow FF. By moving the implant delivery device 400 in the proximal direction, the cervix C and/or uterus U is straightened, positioned and/or reoriented such that the uterine cavity $U_C$ is more accessible via the cervical opening O. In some embodiments, the implant delivery device 400 can be moved in a proximal direction until a desired level of alignment and/or "straightness" between the uterine cavity and the cervical canal is achieved. For example, in some embodiments, the implant delivery device 400 can be moved in a proximal direction until an angle Θ between a center line $CL_O$ of the cervical canal and/or the cervical opening O and a center line $CL_C$ of the uterine cavity of the uterus is greater than approximately 90 degrees. In other embodiments, the implant delivery device is moved proximally until the angle between the uterine cavity and the cervical canal is greater than approximately 115 degrees, 135 degrees, 150 degrees or 165 degrees.

After the cervix C and/or uterus U is straightened, positioned and/or reoriented, the insertion member 461 can be advanced in a distal direction beyond the contact portion 447 and into the uterine cavity $U_C$ to place the implant 401 in any manner of the types described herein. In this manner, the delivery device can both straighten and/or align the target tissue and deliver the implant, thereby obviating the need for a tenaculum.

Although the contact portion 447 is shown and described above as being configured to exert a vacuum force that spatially varies along the external surface S of the cervix C, in other embodiments, the contact portion 447 can be configured to exert a substantially uniform vacuum force along the external surface S of the cervix C. In other embodiments, however, the contact portion 447 can define a additional volumes in fluid communication with the vacuum channel 481 to produce localized and/or noncontiguous areas of vacuum force.

FIGS. 10-19 show an implant delivery device 500 according to an embodiment. The implant delivery device 500 includes a housing 510, an insertion assembly 560, a head 540, and a vacuum assembly 580. The housing 510 includes a proximal end 511 and a distal end 512 and defines a housing passageway 513 therebetween. The housing 510 includes a pair of holders 516 configured to couple the vacuum assembly 580 to the housing 510. The holders 516 can be any suitable holder and can create a friction fit with at least a portion of the vacuum assembly 580. The housing 510 can be any suitable size, shape, or configuration. For example, the 510 is substantially cylindrical with a diameter suitable for insertion into a body orifice. The housing 510 can be substantially tubular and can be formed from any suitable material, such as, for example, a plastic. Additionally, the housing 510 can include a lubricated outer surface to ease in the insertion of the housing into the body.

The proximal end 511 of the housing 510 is coupled to an adapter cap 520. The adapter cap 520 (FIG. 11) includes a proximal end 521 and a distal end 522. The proximal end 521 of the adapter cap 520 includes a barbed fitting 523 and defines a lumen (not shown). The barbed fitting 523 can be coupled to a source of pressurized fluid (not shown in FIGS. 10-19). For example, in some embodiments, the source of pressurized fluid can be an air bladder with an air delivery tube. In such embodiments, the barbed fitting 523 can be inserted into the air delivery tube to place the housing passageway in fluid communication with the source of pressurized fluid, via the lumen, as describe in further detail herein. While shown in FIG. 11 as including a barbed fitting 523, the adapter cap 520 can include any suitable fitting configured to couple to any suitable energy storage device and/or source of pressurized fluid.

The distal end 522 of the adapter cap 520 includes a center protrusion 524 that include a set of sealing members 525. In this manner, the center protrusion 524 can be inserted into the proximal end of the housing passageway 513. The sealing members 525 define a friction fit with the inner walls of the housing 510, such that the sealing members 525 produce a fluid-tight seal with the proximal end 511 of the housing 510.

The insertion assembly 560 (FIG. 12) is, at least partially, disposed within the housing passageway 513 and can be configured to move distally within the housing 510, in response to a force and/or pressure applied by source of pressurized fluid (not shown in FIGS. 10-19). The insertion assembly includes a first insertion member 561 and a second insertion member 566, and an actuator tube 575. The first insertion member 561 includes a proximal end portion 562 and a distal end portion 563, and defines a lumen 564 therebetween. The proximal end portion 562 of the first insertion member 561 is fixedly coupled to a plunger 565. The first insertion member 561 can be any suitable shape, size, or configuration and can be formed from any suitable material. In some embodiments, the first insertion member 561 can be formed from a flexible polymer. In other embodiments, the first insertion member 561 can be formed from a plastic, a rubber, and/or a combination of materials.

The plunger 565 can be any suitable plunger configured to produce a fluid tight seal with the inner walls of the housing passageway 513. The plunger 565 can define any suitable shape and can include any number of sealing members, protrusions, contours, and/or the like. In this manner, a proximal end of the plunger 565, the inner walls of the housing passageway 513, and the adapter cap 520 collectively define a chamber 514 configured to receive a pressurized fluid from the source of pressurized fluid.

The actuator tube 575 includes a proximal end 576 and a distal end 577 and defines a lumen 578 therebetween. The distal end 577 of the actuator tube 575 is fixedly coupled to the proximal end of the plunger 565. In this manner, the lumen 564 defined by the first insertion member 561 and the lumen 578 defined by the actuator tube 575 collectively define a passageway (not shown in FIGS. 10-19) configured to house at least a portion of the second insertion member 566.

The second insertion member 566 includes a proximal end 567 and a distal end 568. The second insertion member 566 can be any suitable shape, size, or configuration and can be formed of any suitable material, such as, for example, those described with respect to the first insertion member 561. The proximal end 567 is fixedly coupled to a plunger 569 and is disposed within in the actuator tube 575. The plunger 569 can be any suitable plunger configured to produce a fluid tight seal with the inner walls of the actuator tube 575. The distal end of the second insertion member 566 is configured to be removably coupled to an implant, such as, for example, an IUD. In this manner, the second insertion member 566 is configured to move relative to the first insertion member 561 to deliver the implant, as described in further detail herein.

Figure 14:
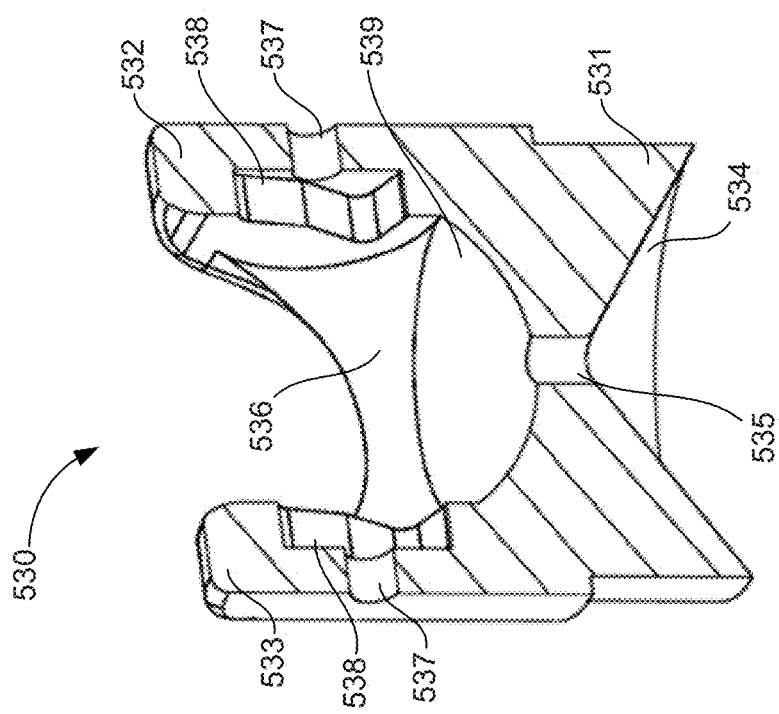
FIG. 14 is a cross-sectional view of the articulation neck of FIG. 13.
Figure 13:
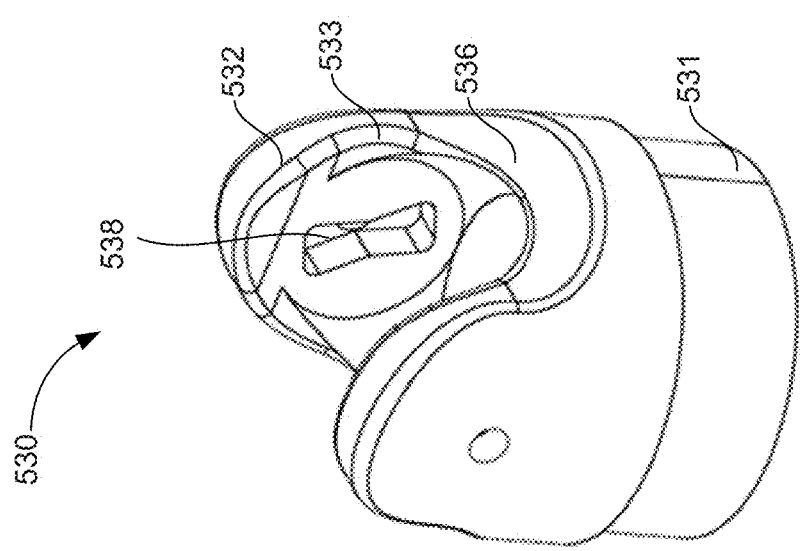
FIG. 13 is a perspective view of an articulation neck included in the implant delivery device of FIG. 10.

The distal end 512 of the housing 510 is coupled to an articulation neck 530 (FIGS. 13 and 14). The articulation neck 530 includes a proximal end 531 and a distal end 532 and defines a neck passageway 535. The proximal end 531 is configured to be inserted into the distal end portion 512 of the housing 510. The proximal end 531 of the articulation neck 530 can produce a friction fit with the inner walls of the housing 510. While shown in FIG. 13 as substantially smooth, the proximal end 531 can include any suitable surface feature and/or texture to facilitate being coupled within the distal end portion 512 of the housing 510. In some embodiments, the proximal end 531 can include a set of sealing protrusions, substantially similar to the sealing protrusions 525 described with respect to the adapter cap 520. The proximal end 531 of the articulation neck 530 defines an engagement portion 534 configured to selectively engage at least a portion of the insertion assembly 560. More specifically, the engagement portion 534 is configured to engage the plunger 565, when the insertion member 560 is moved in a distal direction. This arrangement limits the movement of the first insertion member 561, relative to the housing 510. The engagement portion 534 can be any suitable portion and can include a contour substantially similar to the contour of the distal end of the plunger 565.

Figure 10:
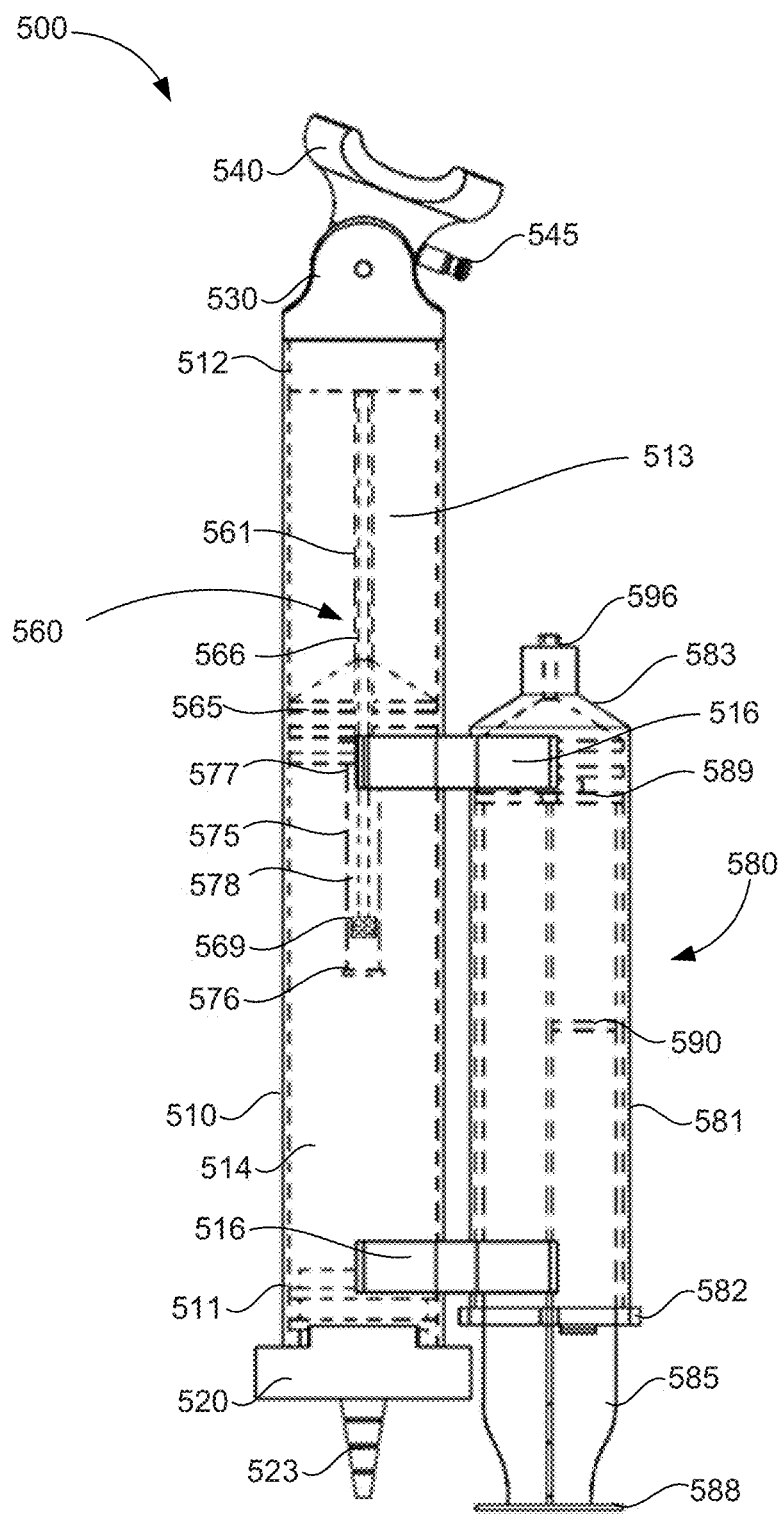
FIG. 10 is a front view of an implant delivery device, according to an embodiment.
Figure 11:
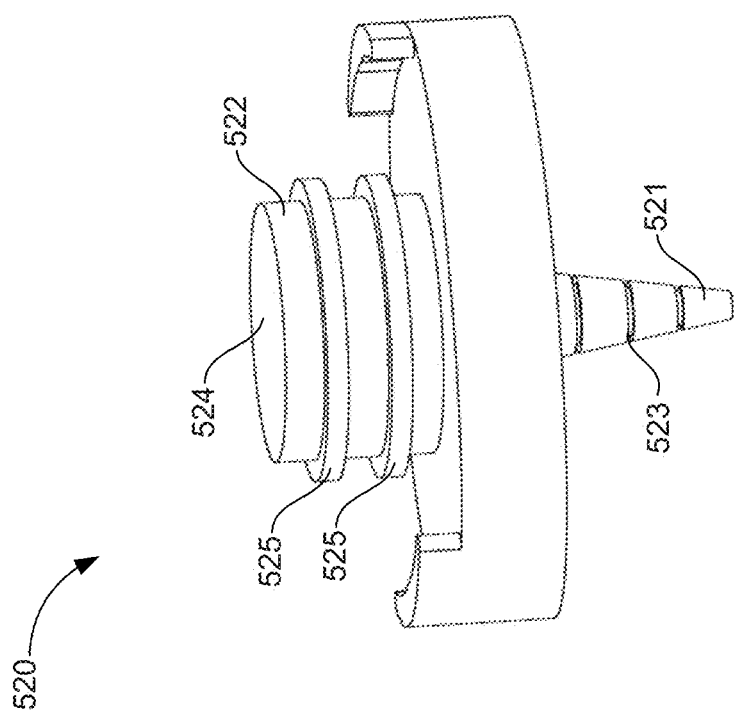
FIG. 11 is a perspective view of a proximal end cap included in the implant delivery device of FIG. 10.

The distal portion 532 of the articulation neck 530 includes a set of sidewalls 533 and is moveably coupled to the head 540 (FIG. 10). The sidewalls 533 can define any suitable shape or configuration. For example, as shown in FIG. 13, the sidewalls 533 define a surface that includes a pair of notches 536. The notches 536 allow for the articulation of the head 540 relative to the housing 510, as described in further detail herein. The sidewalls 533 define a set of apertures 537 and notches 538. The apertures 537 and the notches 538 are disposed opposite each other, and are configured to moveably couple at least a portion of the head 540 to the articulation neck 530.

Figure 16:
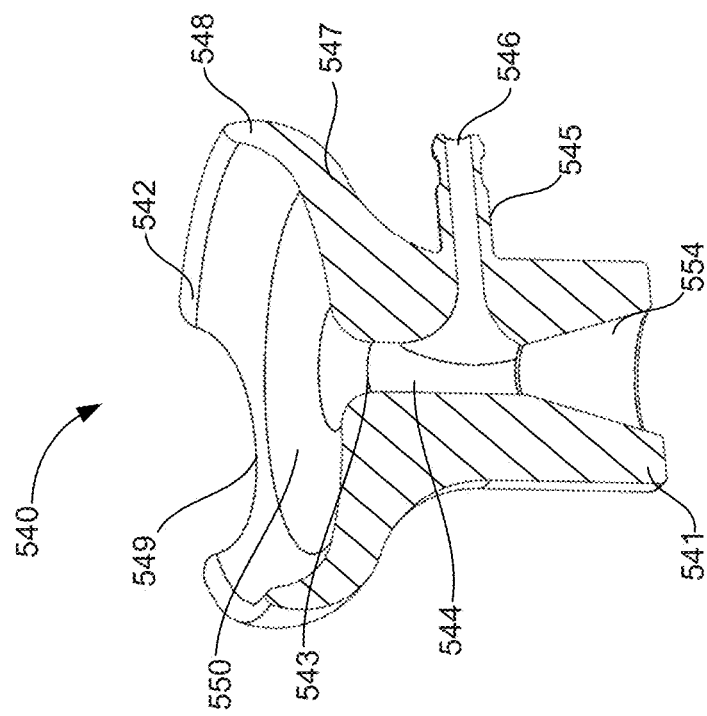
FIG. 16 is a cross-sectional view of the head of FIG. 15.
Figure 15:
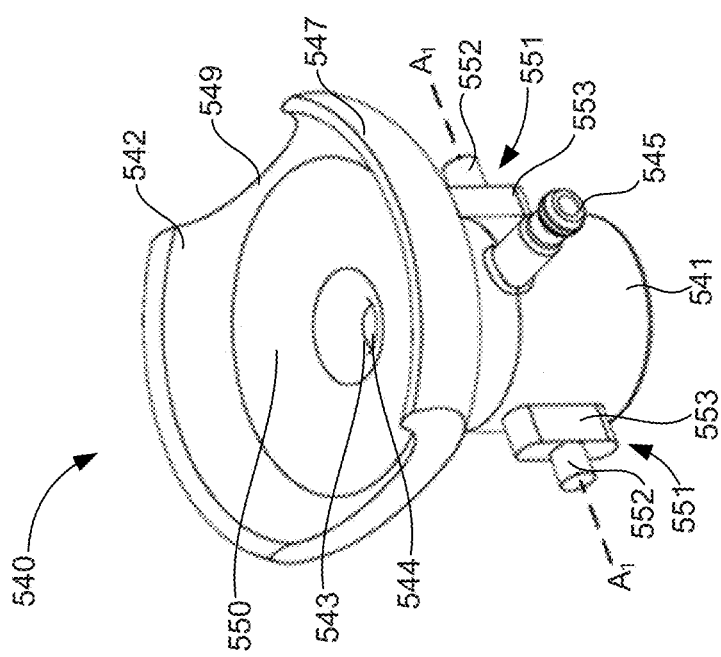
FIG. 15 is a perspective view of a head included in the implant delivery device of FIG. 10.

The head 540 includes a proximal end 541 and a distal end 542 and defines a head passageway 544 therebetween, as shown in FIGS. 15 and 16. The proximal end 541 of the head 540 includes a set of articulation protrusions 551 that moveably couple the head 540 to the articulation neck 530. More specifically, the protrusions 551 are configured to be inserted into the notches 538 and the apertures 537 defined by the sidewalls 533. A first portion 552 of each protrusion 551 forms a pin that is disposed within the corresponding apertures 537. Thus, the protrusions 551 define an axis $A_1$ about which the head 540 can pivot, relative to the articulation neck 530 and/or housing 510. In addition, the first portion 552 of the protrusions 551 (i.e., the pins) define a friction fit with the surface of the sidewalls 533 that defines the apertures 537. This arrangement prevents the head 540 from pivoting freely within the apertures 537. Similarly stated, the fit defined by the first portion 552 of the protrusions 551 and the apertures 537 produces an amount of friction such as to partially resist the motion of the first portion 552 of the protrusions 551 within the apertures 537. A second portion 553 of each protrusion 551 is configured selectively engages the notches 538 defined by the sidewalls 533 to limit the range of pivoting motion of the head 540, relative to the articulation neck 530 and/or housing 510. For example, the notches 538 (FIG. 14) can form a contour such that when the protrusions 551 are disposed within the apertures 537 and the notches 538, the walls of the contour engage the walls of the second portion 553 of the protrusions 551 to limit the range of motion of the head 540. In some embodiments, the pivoting motion is limited to a range between +/−10°. In other embodiments, the range of motion can be in a range between +/−15°, +/−20°, +/−30°, or more.

The distal end 542 of the head 540 includes a contact portion 547. The contact portion 547 includes a sidewall 548 that defines a volume 550. The contact portion 547 and the sidewall 548 can be any suitable size, shape, and configuration. For example, in some embodiments, the sidewall 548 of the contact portion 547 defines a pair of notches 549. In this manner, the notches 549 can be configured to accept a portion of a contact surface associated with a target tissue. For example, the notches 549 can be configured to accept a portion of a cervix of a uterus, such that the contact portion 547 of the head 540 can be placed in a desired position and/or orientation relative to the cervix. In other embodiments, the sidewall 548 can includes any number of notches 549 and/or define a specific contour configured to receive a portion of a contact surface of a target tissue.

The head 540 includes an inner wall 543 that defines the head passageway 544 and includes a tapered portion 554. At least a portion of the insertion assembly 560 is configured to move within the head passageway 544, to a volume substantially outside the implant delivery device 500. In particular, during use, the first insertion member 561 and the second insertion member 566 collectively move from the housing passageway 513 and through the head passageway 544. In some embodiments, the tapered portion 554 and/or other portions of the inner wall 543 are configured to engage a portion of the insertion assembly 560 to facilitate bending of the insertion assembly 560 when the insertion assembly 560 is moved through the head passageway 544. Similarly stated, at least a portion of the sidewall 543 is configured to reduce snagging of the insertion assembly 560 as it moves through the head passageway 544. In some embodiments, the sidewall 543 can include a curved portion (e.g., having a radius of curvature), a low surface roughness and/or a hardened portion to facilitate movement and/or bending of the insertion assembly 560 in use. This arrangement increases patient comfort during use by facilitating bending of the insertion member 560 within the head 540, rather than within a bodily cavity. Similarly stated, this arrangement reduces the likelihood that a portion of the insertion assembly 560 will engage or otherwise press on a body tissue forming the bodily cavity during use.

The head 540 also includes a vacuum fitting 545 that defines a vacuum channel 546. The vacuum fitting 545 can extend from a surface of the head 540 and have any suitable shape. In some embodiments, the vacuum fitting 545 is configured to receive a vacuum line (not shown in FIGS. 10-19) that it can be operably coupled to the vacuum assembly 580. The vacuum channel 546 is in fluid communication with the neck passageway 544 and therefore, with the volume 550 defined by the contact portion 547, as shown in FIG. 16.

Figure 17:
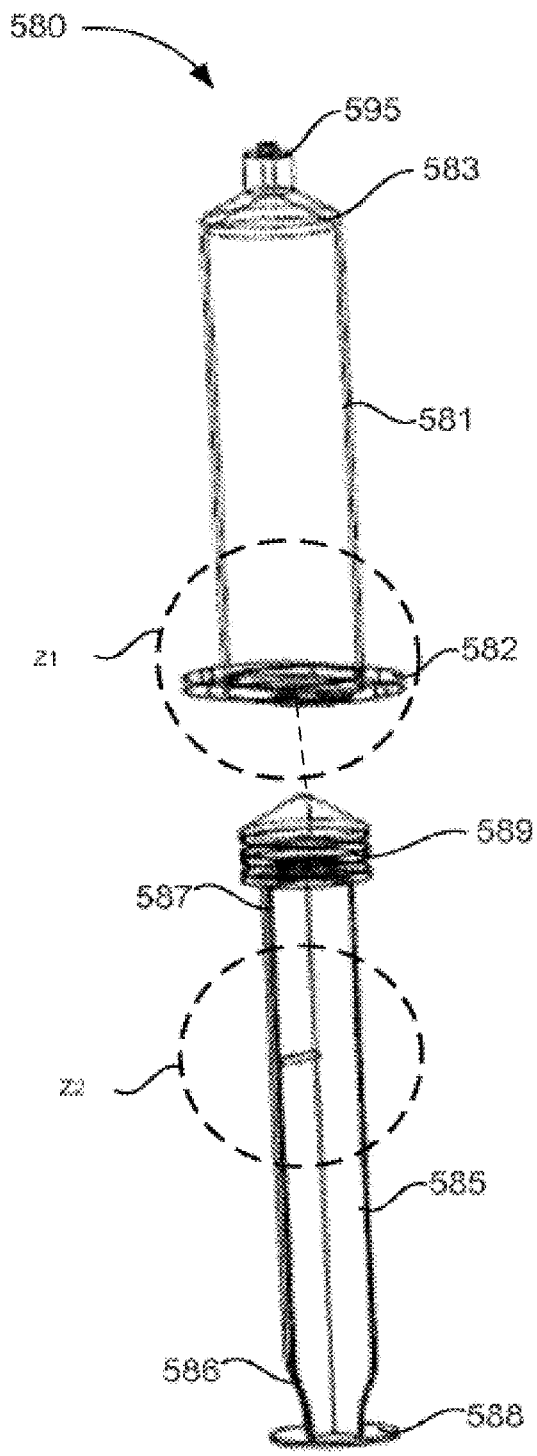
FIG. 17 is an exploded perspective view of a vacuum assembly included in the implant delivery device of FIG. 10.
Figure 19:
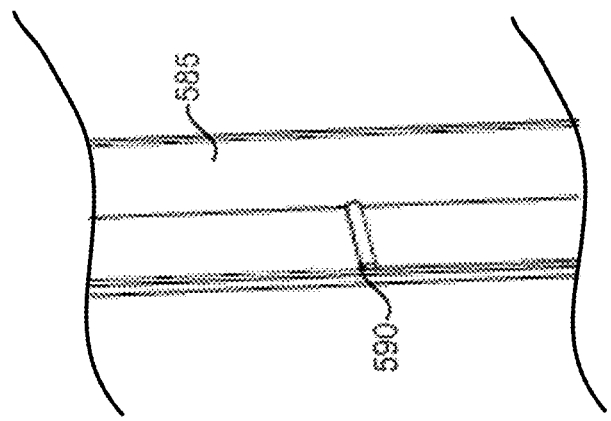
FIG. 19 is an enlarged view of a portion of the vacuum assembly indicated in FIG. 17 by the circle $Z_2$.
Figure 18:
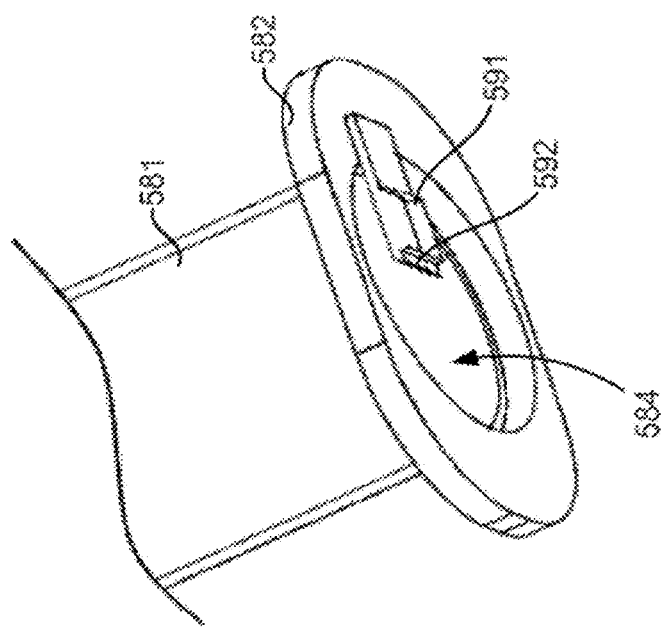
FIG. 18 is an enlarged view of a portion of the vacuum assembly indicated in FIG. 17 by the circle $Z_1$.

The vacuum assembly 580 includes a vacuum tube 581 that houses a vacuum actuator 585 (see e.g., FIGS. 10 and 17). The vacuum tube 580 includes a proximal end 582 and a distal end 583, as shown in FIG. 17. The proximal end 582 is configured to receive at least a portion of the vacuum actuator 585. The distal end 583 includes a vacuum port 595 configured to receive the vacuum line (not shown in FIGS. 10-19) and/or be coupled to the vacuum fitting 545 of the head 540.

The vacuum actuator 585 includes a proximal end 586 and a distal end 587. The proximal end 586 can include a flange 588 configured to be engaged by a physician and/or user. The distal end 587 is fixedly coupled to a plunger 589. The plunger 589 can be substantially similar to any plunger described herein. In this manner, the plunger 589 defines a substantially fluid tight seal with the inner walls of the vacuum tube 581. When disposed within the vacuum tube 581, the plunger 589 and the vacuum tube 581 define a chamber 584 (FIG. 18) that is in fluid communication with the vacuum port 595. In use, the vacuum actuator 585 can be moved in a proximal direction, by the user, thereby increasing the volume of the chamber 584, which produces a negative pressure within the chamber 584. The negative pressure (i.e., vacuum is transmitted through the vacuum line (not shown) to the volume 550 of the head. In this manner, a suction force can be applied to a surface of the body, as described above.

Additionally, the proximal end 582 of the vacuum tube 581 includes a locking tab 591. The locking tab 591 is configured to selectively engage the vacuum actuator 585 to hold the vacuum actuator 585 in the actuated configuration. More specifically, the vacuum actuator 585 includes a ridge 590 (FIG. 19) that selectively contacts an engagement surface 592 of the locking tab 591. The engagement surface 592 contacts the ridge 590 such that the vacuum actuator 585 is in a locked configuration. In this manner, after the vacuum is produced in the chamber 584, the position of the vacuum actuator 585 within the vacuum tube 581 can be maintained, thereby preventing inadvertent loss of vacuum during use of the implant delivery device 500.

When in use, the implant delivery device 500 can be inserted into a bodily lumen of a patient. In some embodiments, the implant delivery device 500 is inserted into a vagina of a patent and through a lumen defined by the walls of the vagina to a cervix of a uterus. The head 540 can pivot, move, and/or rotate, relative to the housing 510, before, during and/or after the implant delivery device 500 passes through the lumen. The contact portion 547 of the head 540 is configured to engage a portion of the cervix. The head 540 can pivot, move, and/or rotate such that the contact portion 547 of the head 540 can substantially circumscribe a contact surface of the cervix. When the head 540 is positioned adjacent the bodily surface (e.g., the outer surface of the cervix), the side walls 548 of the contact portion 547 engage the contact surface of the cervix and thus, the side walls 548 and at least a portion of the contact surface substantially enclose the volume 550 of the head 540. In this manner, when the vacuum assembly 580 is actuated the negative pressure within the vacuum chamber 584 can exert a suction force through the vacuum line (not shown in FIGS. 10-19), into the volume 550, and subsequently on the contact surface of the cervix.

When the suction force is exerted on the contact surface of the cervix, the vacuum actuator 585 can be placed in the locked position (described above in reference to FIGS. 18 and 19). The implant delivery device 500 can be moved to reposition the uterus into a desired position, orientation and/or configuration by moving the implant delivery device 500 in the proximal direction, as described above with reference to FIGS. 7-9.

When the uterus and/or cervix are in the desired position, the insertion assembly 560 can be actuated to deliver the implant. In particular, a source of pressurized fluid can be actuated and/or placed in fluid communication with the proximal end 511 of the housing 510. In some embodiments, the source of pressurized fluid can include a manually-actuated air bulb, an air tube, and a control valve. In such embodiments, the air tube is coupled to the ribbed fitting 523 included in the adapter cap 520. In this manner, the air bulb can be actuated to convey a pressurized fluid into the chamber 514, which exerts a force to move the insertion assembly 560 in the distal direction. In other embodiments, the source of pressurized fluid can include an energy storage member, such as a compressed gas container, a propellant cartridge, chemical energy storage member or the like, which produces the pressurized fluid automatically when actuated by the user. In yet other embodiments, the force to produce the insertion can be produced by any other suitable energy storage member, such as, for example, a spring.

Figure 12:
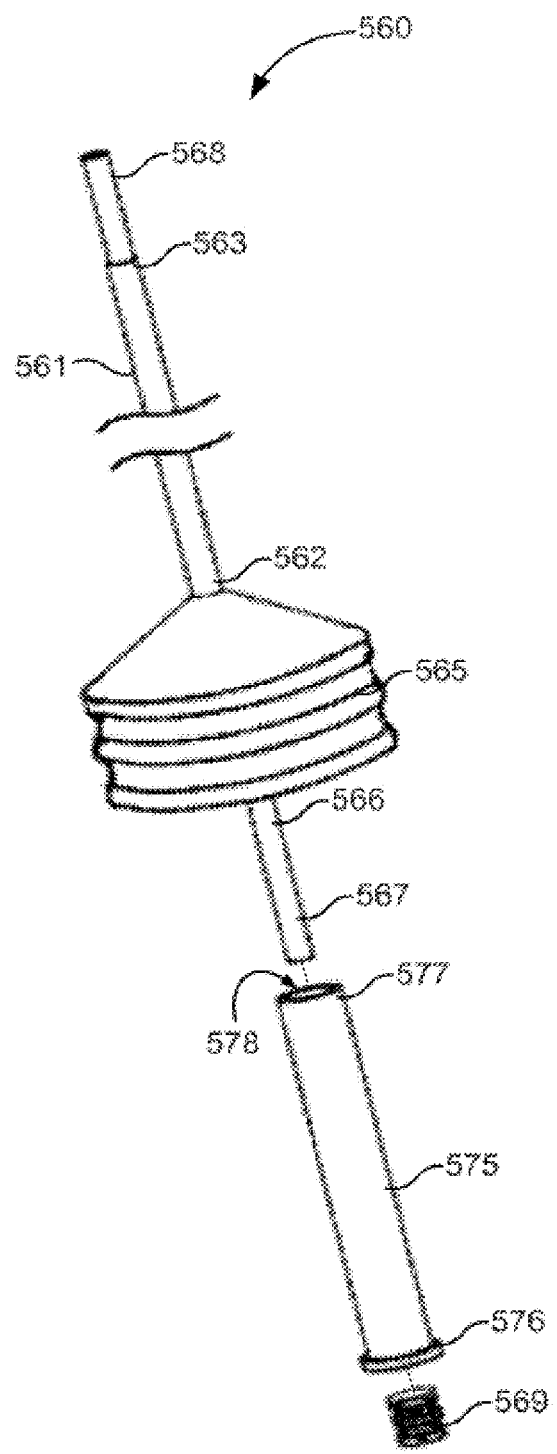
FIG. 12 is an exploded perspective view of an insertion assembly included in the implant delivery device of FIG. 10.

As shown in FIGS. 10 and 12, the plunger 565 defines a larger surface area than does the plunger 569. Since the force exerted on each plunger is directly proportional to the area of the plunger, when the pressurized fluid is conveyed into the chamber 514, the force exerted on the plunger 565 is greater than the force exerted on the plunger 569. Thus, the force exerted by the pressurized fluid moves the plunger 565 in the distal direction within the housing 510. Because the actuator tube 575 and the first insertion member 561 are fixedly coupled to the plunger 565, the insertion assembly 560 collectively moves with the plunger 565 in the distal direction. In this manner, at least a portion of the first insertion member 561 and the second insertion member 566 can move within the housing passageway 513 and through the neck passageway 535 and the head passageway 544. This operation can be referred to as the "first insertion operation."

The plunger 569 and the actuator tube 575 are collectively configured such that the force exerted by the pressurized fluid on the plunger 569 during the first insertion operation (which, as discussed above, is lower than the force exerted on the plunger 565) is insufficient to move the plunger 569, and therefore the second insertion member 566, within the actuator tube 575. Thus, during the first insertion operation, the distal end portion 568 of the second insertion member 566, and thus, the implant (not shown) is maintained within the first insertion member 561.

The engagement portion 534 can contact the plunger 585 to limit the movement of the first insertion member 561, relative to the housing 510 during the first insertion operation. Thus, the first insertion member 561 is configured to be moved a predetermined distance (e.g., a minimum anatomical depth associated with the uterus) during the first insertion operation. In some embodiments, the insertion assembly 560 and the engagement portion 534 can be configured such that the first insertion member 561 can extend approximately 5 cm beyond the contact portion 547 of the head 540. In other embodiments, the first insertion member 561 can extend any suitable distance great than or less than 5 cm.

When the plunger 565 is in contact with the engagement portion 534, the pressure of the pressurized fluid in the chamber 514 can continue to increase. In some embodiments, the user can manually actuate the air bulb to produce an increased pressure within the chamber 514. In other embodiments, the energy storage member can be actuated a second time to produce an increased pressure within the chamber 514. The pressure can be increased until the force exerted on the plunger 569 of the second insertion member 566 is sufficient move the second insertion member 566 in the distal direction, relative to the first insertion member 561. This operation can be referred to as the "second insertion operation." During the second insertion operation, the implant (not shown) is decoupled from and/or pushed out of the first insertion member 561 and into a desired position within the uterus.

In some embodiments, the implant delivery device 500 can include a valve or other control mechanism configured to regulate the pressure within the chamber 514 during the first insertion operation and/or the second insertion operation such that the force exerted by second insertion member 566 on the implant is limited. In this manner, the second insertion member 566 can enter a uterine cavity through a cervical os and deliver the implant (e.g., IUD) to the target tissue within the uterus.

Although the implant delivery device 500 is shown and described above as including two plungers configured to produce a first insertion operation that is distinct from a second insertion operation, in other embodiments, a device can include a single plunger configured to produce a two-stage delivery. FIGS. 20-24 show an implant delivery device 600 according to an embodiment. The implant delivery device 600 includes a housing 610, source of pressurized fluid 603, and a head 640. The housing 610 includes a proximal end 611 and a distal end 612 and defines a housing passageway 613 and a vacuum channel 684. The housing 610 can be any suitable shape, size, or configuration, as described herein. For example, the housing 610 can be substantially cylindrical with a diameter suitable for insertion into a body orifice. The distal end 612 of the housing 610 is rotatably coupled to the head 640.

The head 640 can be coupled to the distal end 612 of the housing 610 in any suitable way. For example, the distal end 612 of the housing 610 can include a fitting, cap, joint, and/or the like configured to rotatably couple the head 640 to the housing 610. In some embodiments, the housing 610 and the head 640 are coupled via a sleeve and/or the like (not shown in FIGS. 20-24). The head 640 defines a head passageway and includes a contact portion 647 that defines a volume 650. The head 640 can be any suitable shape, size, or configuration. For example, as shown in FIG. 20, the head 640 can substantially form a cup shape. The housing passageway 613 and the head passageway can collectively define an insertion passageway 605 that can be substantially nonlinear, such that at least a portion of the insertion passageway 605 bends and/or curves.

The implant delivery device 600 can be inserted into a bodily lumen defined by the body of a patient, such as, for example, the lumen defined by the inner walls of the vagina. With the implant delivery device 600 inserted into the lumen, the contact portion 647 contacts a surface associated target tissue, such as, for example, a cervix of a uterus. The contact portion 647 can be configured to substantially circumscribe a surface associated with a target tissue. For example, when the contact portion 647 is in contact with the contact surface of the cervix, the walls of the contact portion 647 substantially surround a cervical opening. In this manner, at least a portion of the contact surface and the contact portion 647 substantially enclose the volume 650.

The vacuum channel 684 defined by the housing 610 includes a proximal end 682 and a distal end 683. The distal end 683 includes a vacuum port 695 and is in fluid communication with the insertion passageway 605. In this manner, the vacuum channel 684 is configured to be in fluid communication with at least a portion of the volume 650. A vacuum actuator 685 is disposed at least partially within the vacuum channel 684, and can be manually actuated to form a vacuum within the vacuum channel 684. The actuator 685 includes a plunger 689 configured to form an airtight seal with the inner surface of the vacuum channel 684. Therefore, in use, the actuator 685 can be retracted (e.g., moved in a proximal direction) to produce a vacuum force. With the vacuum channel 684 in fluid communication with at least a portion of the volume 650 and with the contact surface substantially enclosing the volume 650, as described above, a suction force can be exerted on the contact surface associated with the target tissue.

The implant delivery device 610 further includes a first insertion member 661 and a second insertion member 666. The first insertion member 661 can be any suitable shape, size, or configuration. For example, in some embodiments, the first insertion member 661 can be formed from a flexible material such as a rubber, elastomer, polymer, and/or plastic. The first insertion member 661 includes a proximal end 662 and a distal end 663. In some embodiments, the first insertion member 661 defines an insertion channel between the proximal end 661 and the distal end 662, configured to receive at least a portion of the second insertion member 666.

The second insertion member 666 includes a proximal end 667 and a distal end 668. Similar to the first insertion member 661, the second insertion member 666 can be any suitable size, shape, or configuration, and can be formed from any suitable material. The proximal end 667 is at least partially disposed within the housing passageway 613. The distal end 668 is configured to be removably coupled to an implant 601. In some embodiments, the implant 601 is an intrauterine device (IUD) configured to be implanted into a target portion of a uterus of a patient. At least a portion of the first insertion member 661 and the second insertion member 666 are configured to move relative to the housing 610 within the housing passageway 613 to deliver the implant 601. Similarly, at least a portion of the second insertion member 666 is configured to move relative to the first insertion member 661 within the insertion channel 664.

FIG. 21 shows the implant delivery device 600 in a second configuration (i.e., at the end of a first insertion operation), in response to a force being applied by the source of pressurized fluid 603. The source of pressurized fluid 603 can include an air bulb 608, an air tube 607, and a control valve 602. The air tube 607 is coupled to the proximal end 612 of the housing 610 using any suitable fitting, coupling, adapter, and/or the like. In this manner, when the air bulb 608 is actuated (i.e., squeezed) a pressurized fluid can be conveyed into the housing passageway 613 to move the first insertion member 661 and the second insertion member 666 in the distal direction. More specifically, the force exerted by the pressurized fluid moves the plunger 669 of the second insertion member 666 in the distal direction. The second insertion member 666 and the first insertion member 661 are collectively configured such that the force exerted by the pressurized fluid on the plunger 569 during the first insertion operation is insufficient to move the second insertion member 566 within the first insertion member 661. Thus, during the first insertion operation, the second insertion member 566 and the first insertion member 661 collectively move relative to the housing 610 to move the device 600 from the first configuration (FIG. 20) to the second configuration (FIG. 21). Thus, during the first insertion operation, the distal end portion of the second insertion member 666, and thus, the implant 601, is maintained within the first insertion member 661.

The housing 610 includes an engagement portion 634 configured to selectively engage the first insertion member 661. In this manner, the first insertion member 661 can extend a predetermined distance beyond the contact portion 647 of the head 640 when in the second configuration (i.e., upon completion of the first insertion operation), as shown in FIG. 21.

Figure 22:
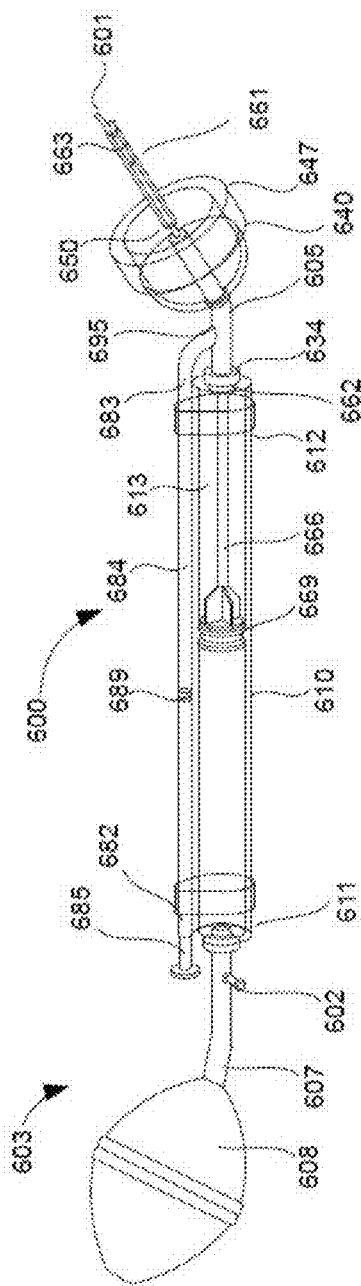
Figure 23:
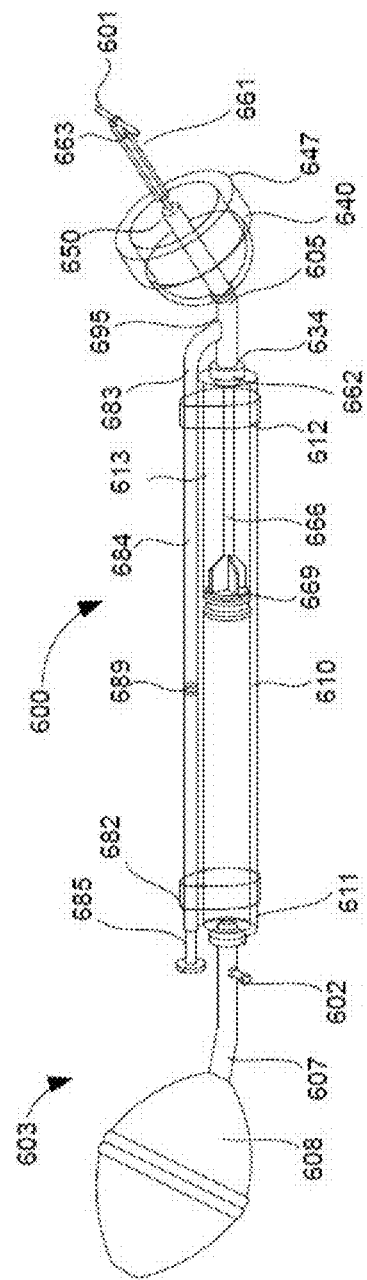
Figure 24:
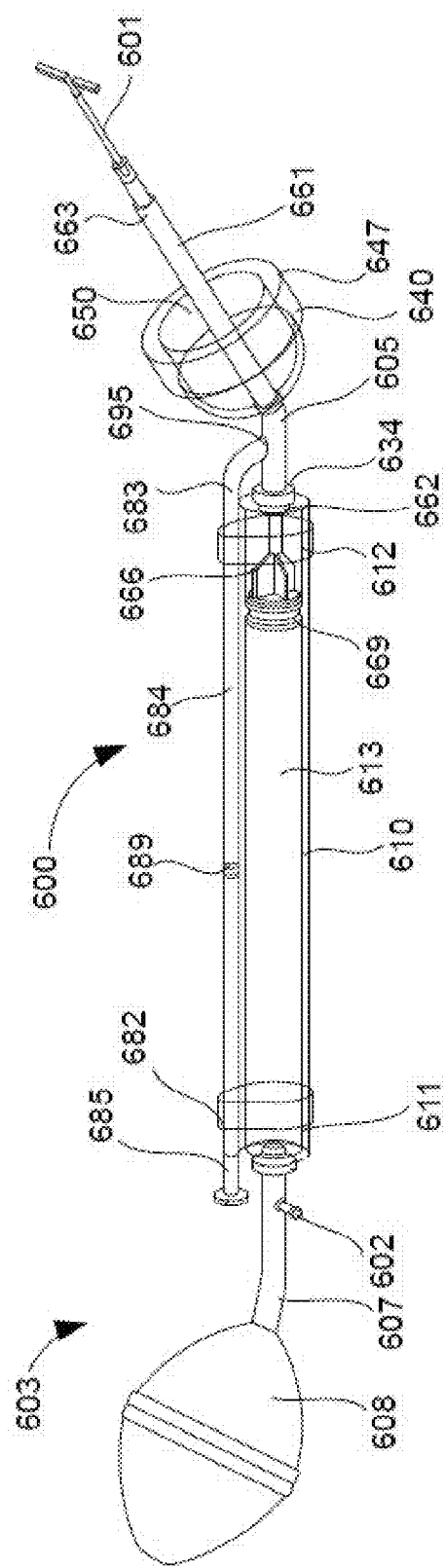

With the first insertion member 661 in contact with the engagement portion 634, the pressurized fluid in the housing passageway 613 continues to exert at the force on the plunger 669 of the second insertion member 666 to move the second insertion member 666 in the distal direction, relative to the first insertion member 661 (FIGS. 22-24). The valve 602 included in the energy storage member 603 can be used to regulate the pressure within the housing passageway 613 such that the force exerted by second insertion member 666 on the implant is limited. In this manner, the second insertion member 666 can enter a uterine cavity and deliver the implant 601 (e.g., IUD) to the target tissue as shown in FIG. 24.

Figure 25:
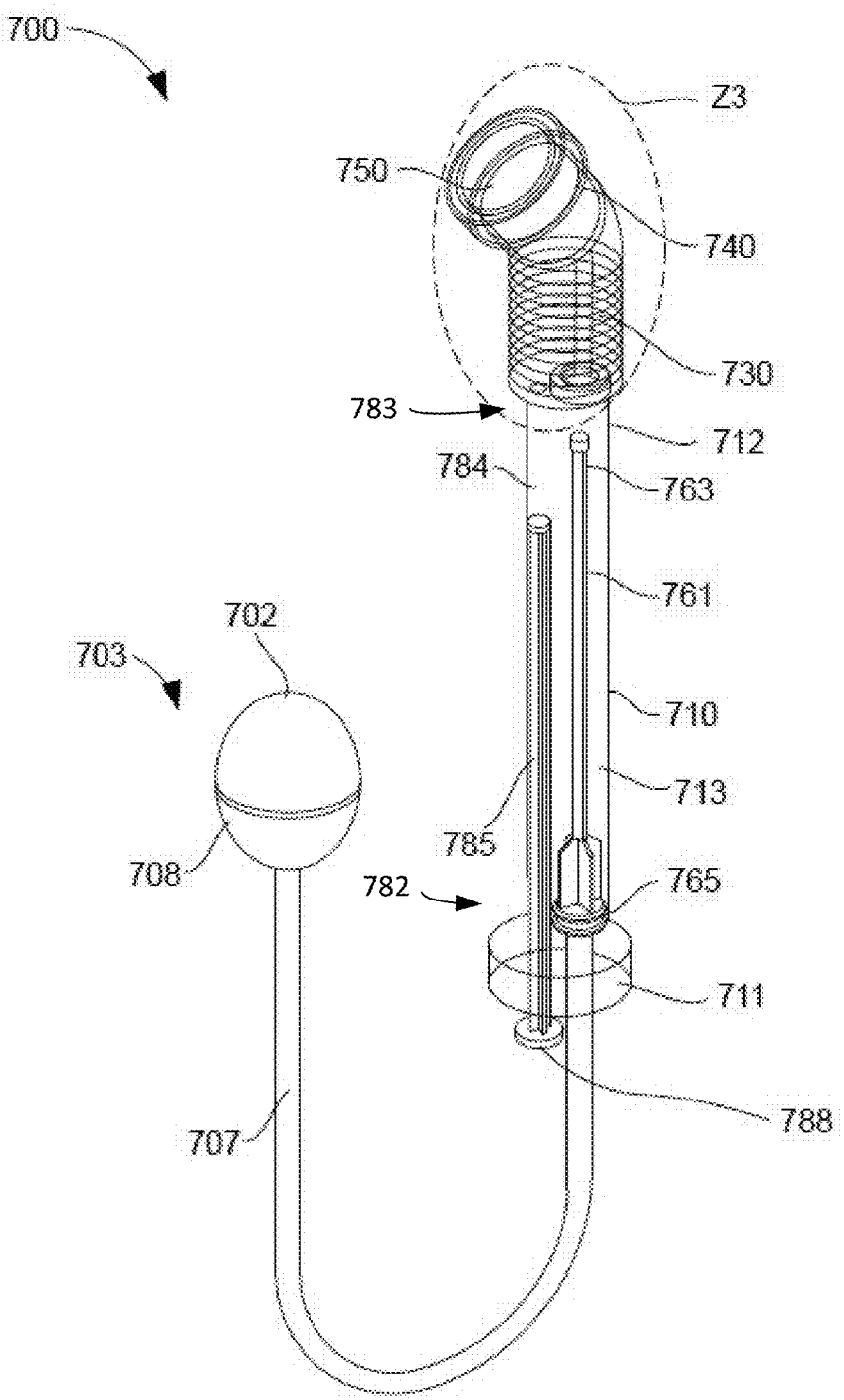
FIG. 25 is a perspective view of an implant delivery device according to an embodiment.
Figure 26:
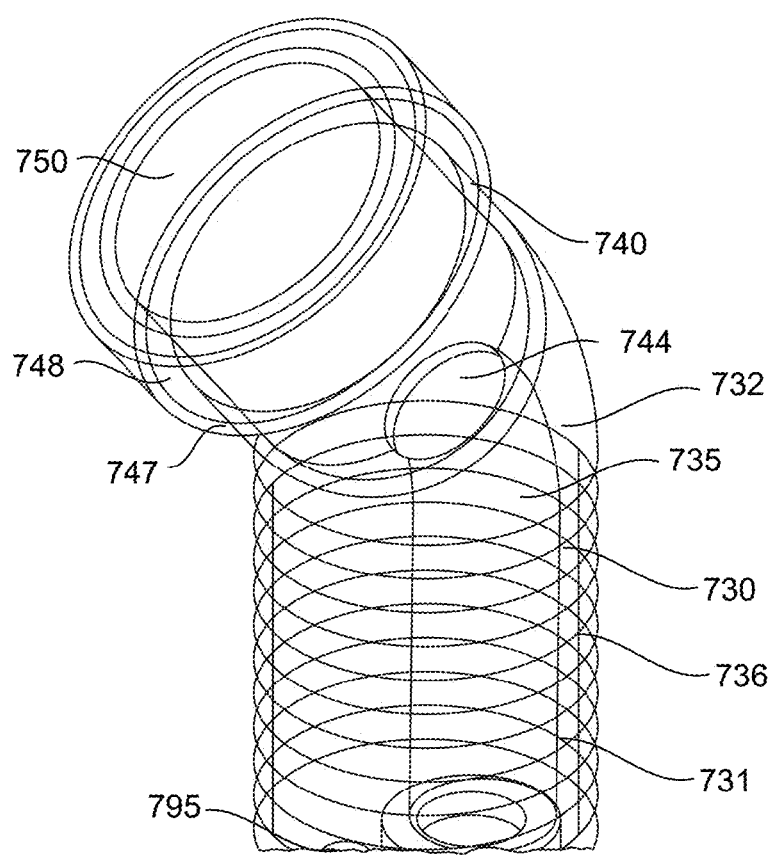
FIG. 26 is an enlarged view of a portion of the implant delivery device indicated in FIG. 25 by the region identified as $Z_3$.
Figure 27:
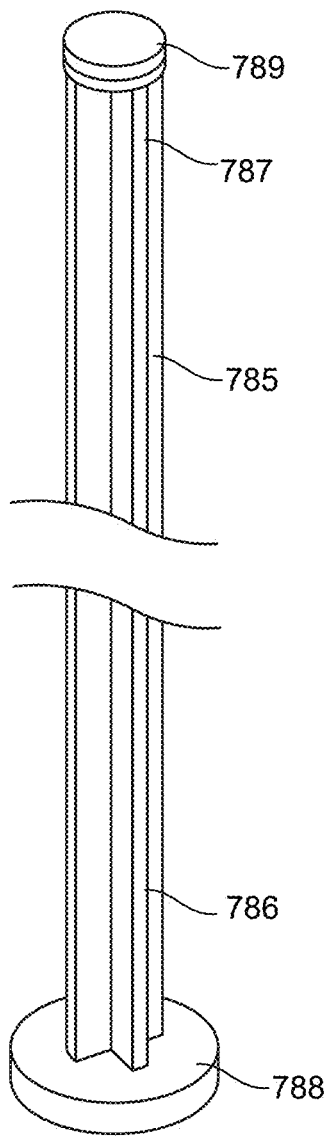
FIG. 27 is a perspective view of a vacuum actuator included in the implant delivery device of FIG. 25.

FIGS. 25-32 show an implant delivery device 700 according to an embodiment. The implant delivery device 700 includes a housing 710, a source of pressurized fluid 703, and a head 740 (FIG. 26). The housing 710 includes a proximal end 711 and a distal end 712, and defines a housing passageway 713 and a vacuum channel 784. The housing 710 can be any suitable shape, size, or configuration, as described herein. For example, the housing 710 can be substantially cylindrical with a diameter suitable for insertion into a body orifice. The distal end 712 of the housing 710 is rotatably coupled to the head 740.

The head 740 can be coupled to the distal end 712 of the housing 710 in any suitable way. For example, the distal end 712 of the housing 710 can couple to the head 740 via a neck 730 (FIG. 26). The neck 730 includes sidewalls 736 that define a set of ribs allowing for rotational motion of the head 740. In some embodiments, the neck 730 is formed of a flexible material, such as, for example, a rubber or a polymer. The neck 730 defines a neck passageway 735 between a proximal end 731 and a distal end 732. Similarly, the head 740 defines a head passageway 744 and includes a contact portion 747. The contact portion 747 includes a sidewall 648 that defines a volume 750. The head 740 can be any suitable shape, size, or configuration. For example, as shown in FIG. 26, the head 740 can substantially form a cup shape. The housing passageway 713, the neck passageway 735, and the head passageway 744 collectively define an insertion passageway (not identified) that can be substantially nonlinear, such that at least a portion of the insertion passageway bends and/or curves during an insertion operation.

The implant delivery device 700 can be inserted into a bodily lumen defined by the body of a patient, such as, for example, the lumen defined by the inner walls of the vagina. With the implant delivery device 700 inserted into the lumen, the contact portion 747 contacts a surface associated target tissue, such as, for example, a cervix of a uterus. The contact portion 747 can be configured to substantially circumscribe a surface associated with a target tissue. For example, when the contact portion 747 is in contact with the contact surface of the cervix, the contact portion 747 substantially surrounds a cervical opening. In this manner, at least a portion of the contact surface and the contact portion 747 substantially enclose the volume 750.

The vacuum channel 784 defined by the housing 710 includes a proximal end 782 and a distal end 783 (FIG. 25). The distal end 783 includes a vacuum port 795 that fluidically coupled to the neck 730 (FIG. 26). In this manner, the vacuum channel 784 is configured to be in fluid communication with at least a portion of the volume 750. A vacuum actuator 785 is movably disposed within the vacuum channel 784, and can be manually actuated to form a vacuum. The vacuum actuator 785 (FIG. 27) includes proximal end 786 and a distal end 787. The proximal end 786 includes a flange 788 that can be grasped by a user in order to actuate the vacuum chamber 784. In some embodiments, the housing 710 can include a locking mechanism (not shown in FIGS. 25-32) configured to engage the flange 788 to maintain the vacuum actuator 785 in an actuated position. The distal end 788 of the vacuum actuator 785 includes a plunger 789 configured to form an airtight seal with the inner surface of the vacuum channel 784. Therefore, in use, the actuator 785 can be retracted (e.g., moved in a proximal direction) to produce a vacuum force. With the vacuum channel 784 in fluid communication with at least a portion of the volume 750 and with the contact surface substantially enclosing the volume 750, as described above, the vacuum channel 784 transfers a suction force on the contact surface associated with the target tissue.

Figure 28:
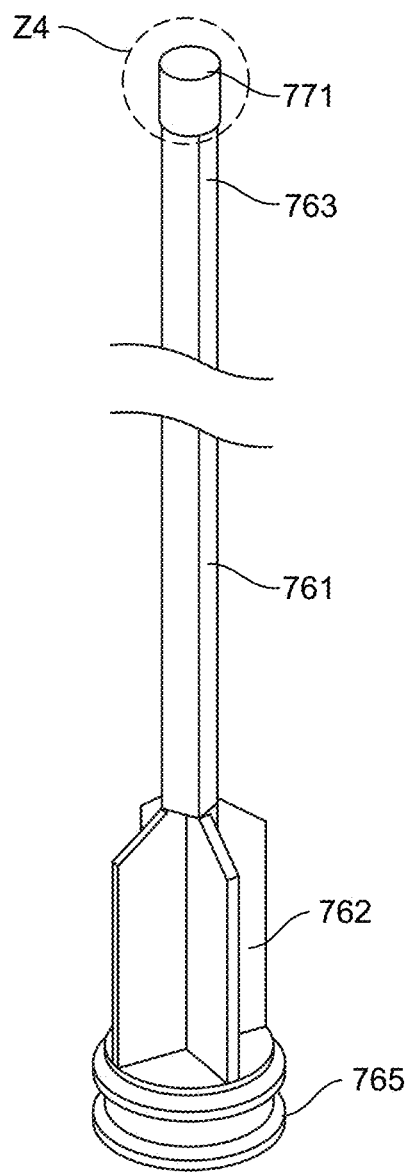
FIG. 28 is a perspective view of an insertion member included in the implant delivery device of FIG. 25.
Figure 29:
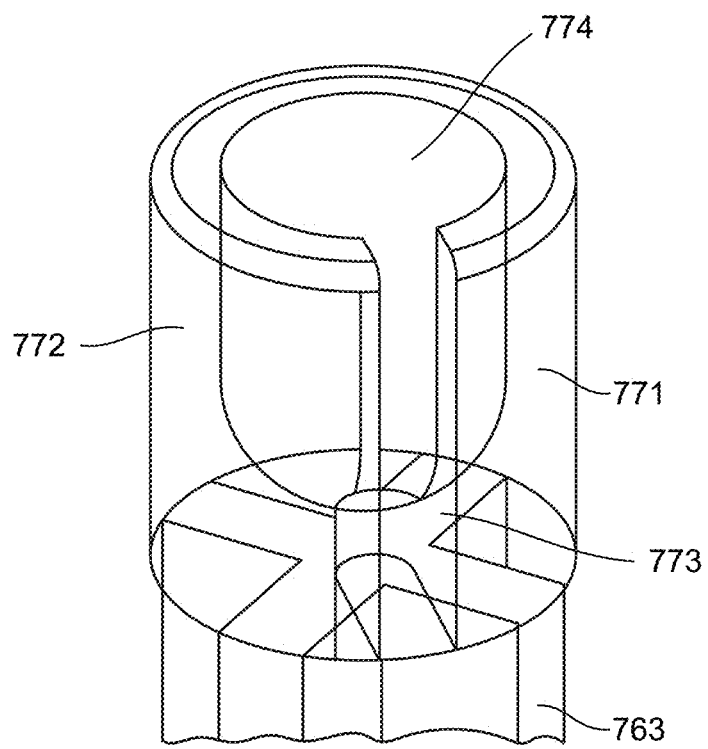
FIG. 29 is an enlarged portion of the insertion member indicated in FIG. 28 by the circle $Z_4$.
Figure 30:
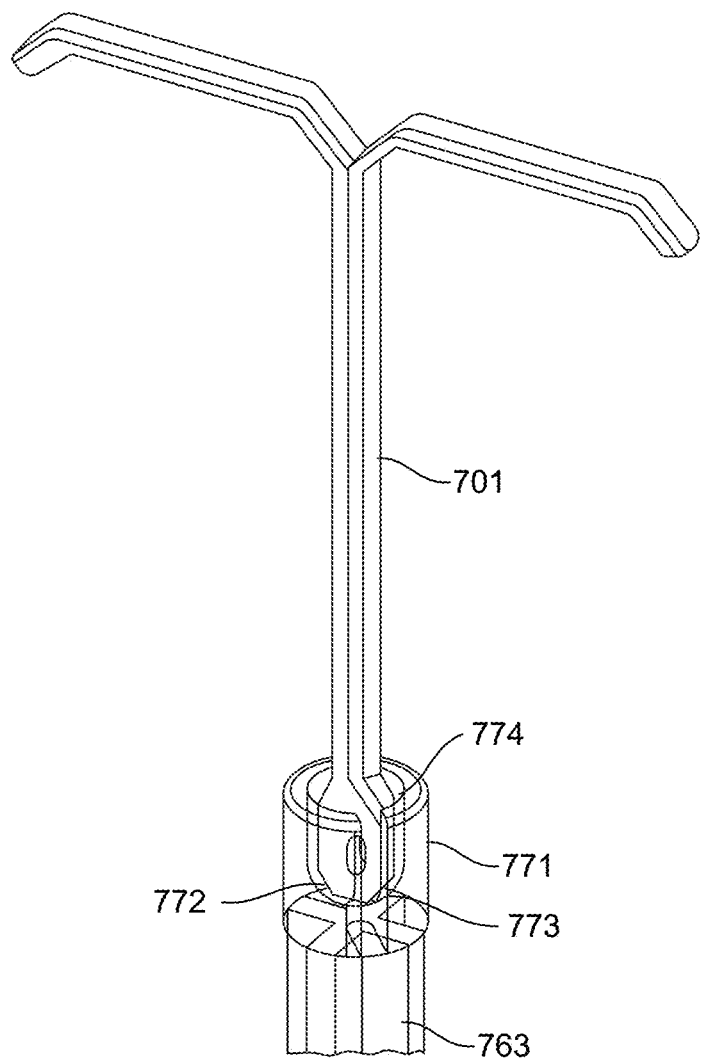
FIG. 30 is a portion of the insertion member of FIG. 28, in use with an intrauterine device.
Figure 31:
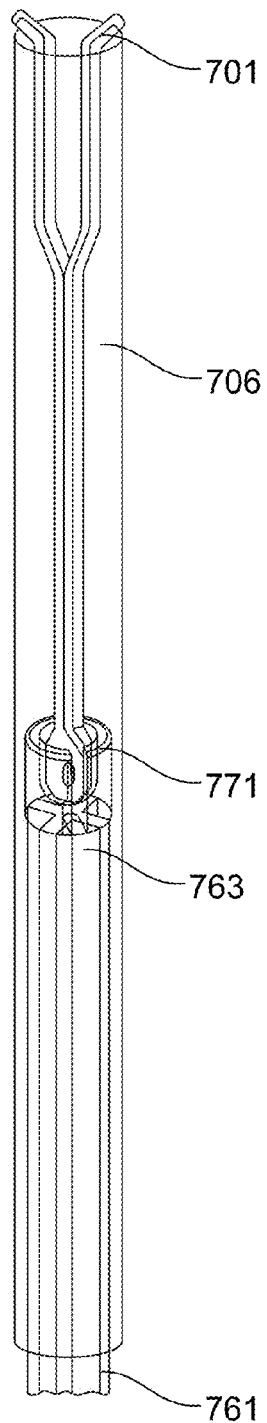
FIG. 31 is a perspective view of a portion of the implant delivery device of FIG. 25, in a first configuration.
Figure 32:
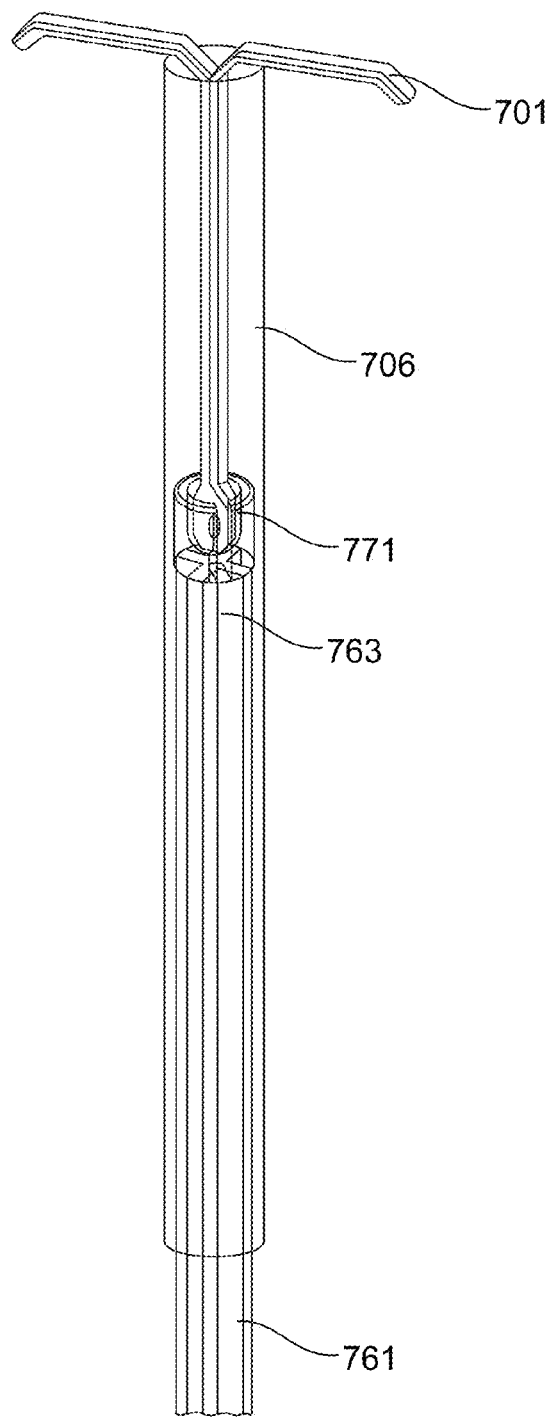
FIG. 32 is a perspective view of the portion of the implant delivery device of FIG. 25, in a second configuration.

The implant delivery device 710 further includes an insertion member 761, as shown in FIG. 28. The insertion member 761 can be any suitable shape, size, or configuration. For example, in some embodiments, the insertion member 761 can be formed from a flexible material such as a rubber, elastomer, polymer, and/or plastic. At least a portion of the insertion member 761 is configured to move relative to the housing 710 within the housing passageway 713. The insertion member 761 includes a proximal end 762 and a distal end 763. The proximal end 762 of the insertion member 761 includes a plunger 765. The distal end 763 includes an articulator 771 that is configured to be removably coupled to an implant 701. In some embodiments, the implant 701 is an intrauterine device (IUD) configured to be implanted into a target portion of a uterus of a patient. As shown in the enlarged view in FIG. 29, the articulator 771 includes a set of sidewalls 772 that define an implant volume 774. The implant volume 774 is configured to receive the implant 701 (FIG. 30). The sidewalls 772 further define a slit 773 configured to receive at least a portion of a string often attached to an IUD. Additionally, the housing 710 includes a retaining tube 706 (see FIG. 31) configured to selectively engage the implant 701. For example, as shown in FIG. 31, the retaining tube 706 maintains an IUD in a collapsed configuration.

The source of pressurized fluid 703 can include an air bulb 708, an air tube 707, and a control valve 702 (FIG. 25). The air tube 707 is coupled to the proximal end 712 of the housing 710 using any suitable fitting, coupling, adapter, and/or the like. In this manner, the air bulb 708 can be actuated and a pressurized fluid can exert a force within the housing passageway 713 to move the insertion member 761 in the distal direction. More specifically, the force exerted by the pressurized fluid moves the plunger 765 of the insertion member in the distal direction. The valve 702 included in the energy storage member 703 can be used to regulate the pressure within the housing passageway 713 such that the force exerted by the insertion member 761 on the implant 701 when the insertion member 761 moves is below a predetermined force. In this manner, a portion of the insertion member 761 can extend beyond the retaining tube 706 (FIG. 32) and enter a uterine cavity to deliver the implant 701 (e.g., IUD) to the target tissue.

Figure 33:
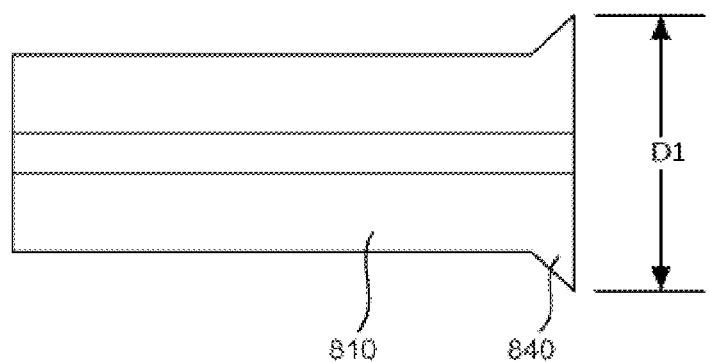
FIG. 33 is a schematic illustration of an implant delivery device according to an embodiment, in a first configuration.
Figure 34:
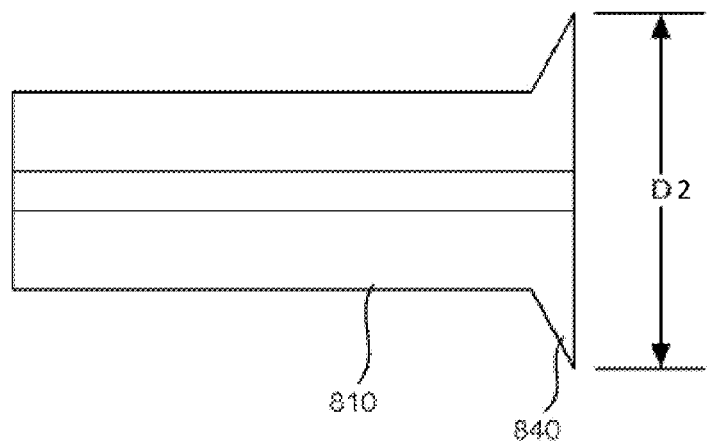
FIG. 34 is a schematic illustration of the implant delivery device of FIG. 33, in a second configuration.

While specific heads and/or contact portions are discussed herein, the components and configurations of the head and/or contact portion can vary. For example, FIG. 33 is a schematic illustration of an implant delivery device 800 in a first configuration that includes a housing 810 and a head 840. The head 840 is rotatably coupled to a distal end of the housing 810 in any suitable manner, such as, for example, those described herein. The head 840 can be any suitable shape, size, or configuration. For example, the head 840 can define a leaflet mechanism that defines a first diameter $D_2$ when in the first configuration. The head 840 can be configured to respond to a force and/or external input that causes the leaflets of the head 840 to expand and or separate when in a second configuration. In this manner, the head 840 can define a second diameter $D_2$, substantially larger than the first diameter, when in the second configuration, as shown in FIG. 34. Similarly stated, the head 840 can be moved between a collapsed configuration, in which the head 840 has a first size (e.g., $D_1$) and an expanded configuration, in which the head 840 has a second size (e.g., $D_2$) larger than the first size.

In some embodiments, an implant delivery device includes one or more mechanical biosensors around the rim of the head and/or the insertion member and a light emitting diode (LED) or other electronic output device at the opposite end of the device. Other indicators can be used instead of an LED, such as for, example, any suitable visual output device (LCD screens, etc.), audible output devices (e.g., a whistle), or mechanical output devices (e.g., haptic output devices).

In some embodiments, an implant delivery device can rotate, bend, and/or move with the cervix and insert the IUD into a woman's uterus with no other tools needed, and without the need for exceptional skill and/or training. The design of the embodiments described herein facilitates ease of use such that after a short training session, any health care provider can properly insert an IUD safely with aseptic technique.

Figure 35:
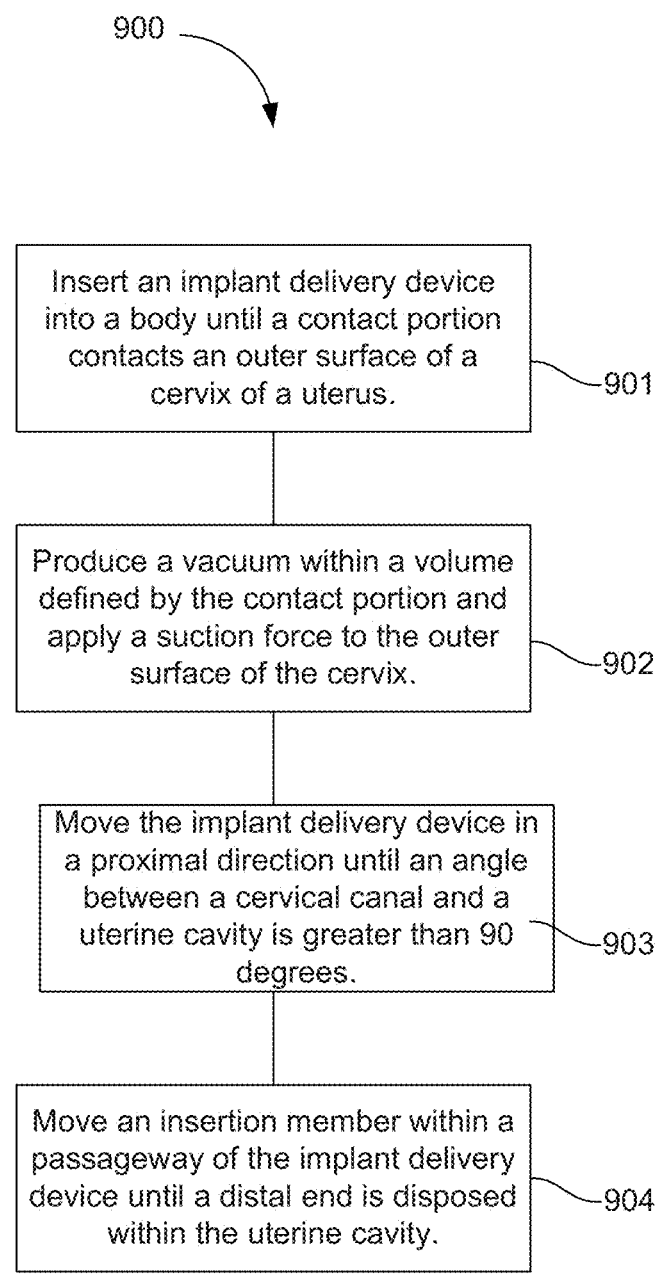
FIG. 35 is a flowchart describing a method of using an implant delivery device, according to an embodiment.

FIG. 35 is a flowchart illustrating a method 900 for implanting and intrauterine device as described herein. The method 900 can be performed using any of the devices shown and described herein. The method 900 includes inserting an implant delivery device into a body until a contact portion included in the implant delivery device contacts an outer surface of a cervix of a uterus, at 901. More specifically, in some embodiments, the contact portion can be similar to the contact portion 547 included in the head 540 that is flexibly coupled to the housing 510 of the implant delivery device 500, described with respect to FIGS. 10-19. The method 900 further includes producing a vacuum within a volume defined by the contact portion and applying a suction force to the surface of the cervix, at 902. For example, in some embodiments, the device can include a vacuum actuator similar to the vacuum actuator 585 that can be pulled in a proximal direction to produce a vacuum within the vacuum chamber 584 to exert a suction force on the surface of the cervix, as described with respect to FIGS. 10-19. With the suction force applied to the surface of the cervix, the implant delivery device is moved in a proximal direction until an angle between a cervical canal of the cervix and a uterine cavity of the uterus is greater than approximately 90 degrees, at 903. In some embodiments, the implant delivery device is moved until the angle between the uterine cavity and the cervical canal is greater than approximately 115 degrees, 135 degrees, 150 degrees or 165 degrees. The method 900 further includes moving an insertion member within a passageway defined by the implant delivery device until a distal end portion of the insertion member is disposed within the uterine cavity, at 904.

Figure 36:
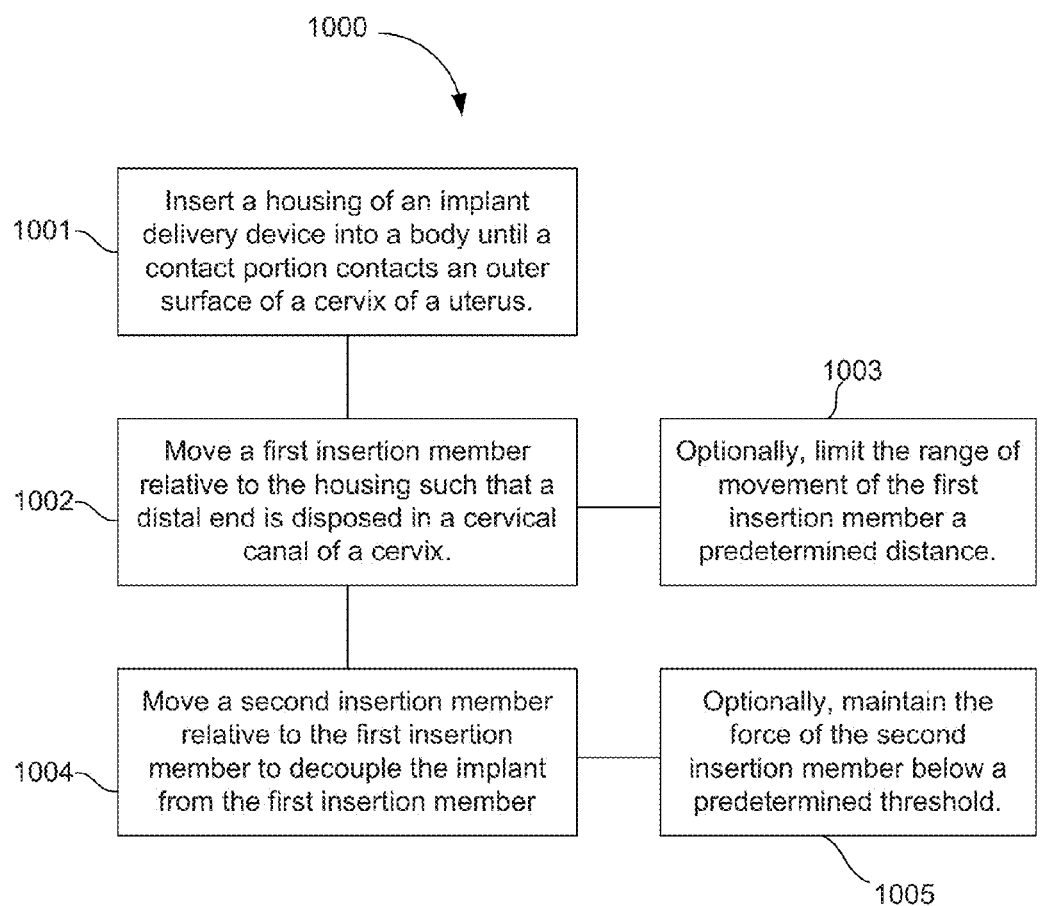
FIG. 36 is a flowchart describing a method of using an implant delivery device, according to an embodiment.

FIG. 36 is a flowchart illustrating a method 1000 for implanting an intrauterine device as described herein. The method 1000 includes inserting an implant delivery device into a body until a contact portion of the implant delivery device contacts an outer surface of a cervix of a uterus, at 1001. More specifically, in some embodiments, the contact portion can be similar to the contact portion 547 included in a head 540 that is flexibly coupled to the housing 510 of the implant delivery device 500, described with respect to FIGS. 10-19. A first insertion member can be moved relative to the housing such that the distal end of the first insertion member is disposed within a cervical canal of the cervix, at 1002. For example, in some embodiments, a first insertion member can be similar to the first insertion member 261, which moves in a distal direction in response to a force from an energy storage member, as described with respect to FIG. 4. In some embodiments, the method 1000 can include limiting the distance the first insertion member can move beyond the contact portion to a predetermined length, at 1003.

The method 1000 further includes moving the second insertion member relative to the first insertion member to decouple the implant from the first insertion member, at 1004. In some embodiments, the method 1000 can include maintaining the force of the second insertion member below a predetermined threshold, at 1005. For example, in some embodiments, the implant delivery device can be similar to the implant delivery device 200, which includes a control member 202 configured to reduce the insertion force $F_1$, such that a portion $F_2$ of the force $F_1$ is transmitted to the second insertion member 266, as described with respect to FIG. 4.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, a device can include a head similar to any of the heads shown and described above, and the head can include a protrusion configured to position the head relative to a lumen defined by the target location. Similarly stated, in some embodiments, an implant delivery device can include a locating protrusion configured to facilitate the alignment and/or positioning of the device with respect to a target location. In some embodiments, the protrusion can define a channel through which an insertion member can be conveyed to deliver an implant.

Although the devices are shown and described herein as delivering an implant through an existing bodily lumen (e.g., an opening and/or canal defined by the cervix), in other embodiments, a device can include a dilator configured to define a bodily lumen and/or expand an existing bodily lumen. In some embodiments, for example, a contact portion of a head includes a dilator configured to dilate a lumen defined by the target location. The dilator can define a channel and/or passageway through which an insertion member can be conveyed to deliver an implant.

In some embodiments, an implant delivery device can include a sleeve configured to be disposed about a head during the insertion operation. The sleeve can be a thin, flexible sleeve, which serves to facilitate insertion of the device and/or maintain sterility during the insertion operation. In some embodiments, an outer surface of the sleeve can include a lubricant.

Although various embodiments have been described as having particular features and/or combinations of components, other embodiments are possible having a combination of any features and/or components from any of embodiments where appropriate. For example, any of the devices shown and described herein can include an articulation neck as described herein. For example, although the implant delivery device 600 shown in FIGS. 20-24 is not shown as including an articulation neck, in other embodiments, an implant delivery device similar to the device 600 can include an articulation neck similar to the articulation neck 730 shown and described above.

What is claimed is:

1. An apparatus, comprising:
a housing defining a housing passageway configured to receive an insertion member, the housing defining a vacuum channel and a vacuum chamber, the vacuum channel in fluid communication with the vacuum chamber;
an actuator at least partially disposed within the vacuum chamber such that movement of the actuator within the vacuum chamber produces a vacuum; and
a head coupled to the housing, the head defining a head passageway in fluid communication with the vacuum channel of the housing, the head including a circular contact portion, the head passageway being centered in the circular contact portion, the circular contact portion configured to contact a surface associated with a cervix of a uterus, the contact portion configured to circumscribe an opening to a bodily cavity associated with the cervix, a side wall of the contact portion defining a volume that is configured to at least partially circumscribe the opening to the bodily cavity such that when the contact portion contacts the surface, the side wall and a portion of the surface substantially enclose the volume, a first end portion of the side wall disposed a first distance from the head passageway, a second end portion of the side wall disposed a second distance from the head passageway, the first distance being different than the second distance, the first end portion of the sidewall being a first point at the most distal end of an outermost circumferential edge of the sidewall and the second end portion of the sidewall being a second point at the most distal end of the outermost circumferential edge of the sidewall, the volume in fluid communication with the head passageway such that when the actuator is moved a vacuum source is exerted on the portion of the surface.

2. The apparatus of claim 1, further comprising:
the insertion member, the insertion member having a distal end portion configured to be removably coupled to an implant, the insertion member configured to move within the housing passageway, in response to a force being exerted on the insertion member, to convey the implant to the uterus via the bodily cavity; and
a control mechanism configured to receive an input force and exert the force on the insertion member, the control mechanism configured to limit a magnitude of the force when the input force exceeds a threshold.

3. The apparatus of claim 2, wherein:
the control mechanism includes a ratchet mechanism or a clutch mechanism.

4. The apparatus of claim 1, wherein the head is configured to rotate relative to the housing with at least one degree of freedom.

5. The apparatus of claim 1, wherein:
the actuator includes a plunger disposed at least partially within the vacuum chamber and configured to form a substantially airtight seal with an inner surface of the vacuum chamber.

6. The apparatus of claim 1, wherein:
the housing includes an engagement portion configured to engage the insertion member to limit movement of the insertion member relative to the housing when at least a portion of the insertion member is disposed within the housing passageway.

7. The apparatus of claim 1, wherein:
the actuator is at least partially disposed outside the vacuum chamber, a portion of the actuator disposed outside the vacuum chamber configured to receive from a user a manual force, the actuator configured to move within the vacuum chamber in response to the manual force received from the user.

8. The apparatus of claim 1, wherein:
the actuator includes a protrusion configured to selectively engage an engagement surface of the vacuum chamber such that axial movement of the actuator relative to the vacuum chamber is limited.

9. The apparatus of claim 1, wherein:
the first point at the most distal end of the outermost circumferential edge of the sidewall is distal to the point at the second most distal end of the outermost circumferential edge of the sidewall.

10. The apparatus of claim 1, wherein:
the outermost circumferential edge of the most distal end of the side wall defines a notch configured to accept a portion of the cervix of the uterus.

11. The apparatus of claim 1, wherein:
the outermost circumferential edge of the most distal end of the side wall defines a discontinuous contour configured to accept a portion of the cervix of the uterus.

12. An apparatus, comprising:
a housing defining a housing passageway configured to receive an insertion member, the housing defining a vacuum channel and a vacuum chamber, the vacuum channel in fluid communication with the vacuum chamber;
an actuator at least partially disposed within the vacuum chamber such that movement of the actuator within the vacuum chamber produces a vacuum; and
a head rotatably coupled to the housing head defining a head passageway in fluid communication with the vacuum channel of the housing, the head having a contact portion configured to contact a surface associated with a target location, a side wall of the contact portion defining a volume that is configured to at least partially circumscribe an opening to a bodily cavity associated with the target location such that, when the contact portion contacts the surface, the side wall and a portion of the surface substantially enclose the volume, an outermost circumferential edge of the most distal end of the side wall defining a discontinuous contour configured to (1) receive a portion of the cervix, and (2) limit movement of the portion of the cervix out of the volume when the portion of the cervix is disposed in the volume, the volume in fluid communication with the head passageway such that when the actuator is moved a vacuum force is exerted on the portion of the surface.

13. The apparatus of claim 12, further comprising:
the insertion member, the insertion member having a distal end portion configured to be removably coupled to an implant, at least a portion of the insertion member disposed within the housing passageway, the insertion member configured to move within the housing passageway, in response to a force being exerted on the insertion member, to convey the implant to the target location via the bodily cavity.

14. The apparatus of claim 13, further comprising:
a control mechanism configured to receive an input force and exert the force on the insertion member, the control mechanism configured to limit a magnitude of the force when the input force exceeds a threshold.

15. The apparatus of claim 14, wherein the control mechanism includes a ratchet mechanism.

16. The apparatus of claim 13, wherein the housing includes an engagement portion configured to engage the insertion member to limit movement of the insertion member relative to the housing.

17. The apparatus of claim 12, wherein:
the actuator includes a protrusion configured to selectively engage an engagement surface of the vacuum chamber such that axial movement of the actuator relative to the vacuum chamber is limited,
the actuator further including a plunger, the plunger configured to be moved within the vacuum chamber to produce the vacuum in the vacuum chamber.

18. The apparatus of claim 17, wherein:
the plunger is configured to be moved from a first position and a second position to produce the vacuum in the vacuum chamber; and
the protrusion configured to engage the engagement surface to maintain the plunger in the second position.

19. The apparatus of claim 12, wherein the head is configured to rotate relative to the housing with at least one degree of freedom.

20. The apparatus of claim 12, wherein the volume is a volume from a plurality of volumes defined by the side wall of the contact portion, each volume from the plurality of volumes in communication with the vacuum channel.

21. The apparatus of claim 12, wherein:
the contact portion of the head defines a discontinuous contour configured to (1) receive a portion of the surface, and (2) limit movement of the portion of the surface out of the volume when the portion of the surface is disposed in the volume.

22. The apparatus of claim 12, wherein the head is rotatably coupled to the housing.

23. The apparatus of claim 12, wherein:
the outermost circumferential edge of the most distal end of the side wall defines a notch.

24. An apparatus, comprising:
a housing defining a housing passageway configured to receive an insertion member, the housing defining a vacuum channel and a vacuum chamber, the vacuum channel in fluid communication with the vacuum chamber;
an actuator at least partially disposed within the vacuum chamber such that movement of the actuator within the vacuum chamber produces a vacuum; and
a head coupled to the housing, the head defining a head passageway in fluid communication with the vacuum channel of the housing, the head including a circular contact portion configured to contact a surface associated with a cervix of a uterus, the contact portion configured to circumscribe an opening to a bodily cavity associated with the cervix, a side wall of the contact portion defining a volume that that is configured to at least partially circumscribe the opening to the bodily cavity such that when the contact portion contacts the surface, the side wall and a portion of the surface substantially enclose the volume, a first point at the most distal end of an outermost circumferential edge of the side wall disposed a first distance from the head passageway, a second point at the most distal end of the outermost circumferential edge of the side wall disposed a second distance from the head passageway, the first distance being different than the second distance, the outermost circumferential edge of the most distal end of the side wall defining a notch configured to accept a portion of the cervix of the uterus, the volume in fluid communication with the head passageway such that when the actuator is moved a vacuum source is exerted on the portion of the surface.

25. The apparatus of claim 24, wherein:
the actuator is at least partially disposed outside the vacuum chamber, a portion of the actuator disposed outside the vacuum chamber configured to receive from a user a manual force, the actuator configured to move within the vacuum chamber in response to the manual force received from the user.

* * * * *